(12) United States Patent
Li

(10) Patent No.: US 7,569,221 B2
(45) Date of Patent: Aug. 4, 2009

(54) COMPOSITIONS AND METHODS FOR IDENTIFYING AGENTS THAT ALTER EXPRESSION OF SURVIVIN

(75) Inventor: Fengzhi Li, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 11/983,652

(22) Filed: Nov. 12, 2007

(65) Prior Publication Data

US 2008/0153101 A1    Jun. 26, 2008

Related U.S. Application Data

(60) Provisional application No. 60/865,254, filed on Nov. 10, 2006.

(51) Int. Cl.
*A61K 48/00*  (2006.01)
*C12N 15/00*  (2006.01)
*C12N 5/00*   (2006.01)
*C12N 5/02*   (2006.01)
*C12N 5/06*   (2006.01)
*C12N 5/10*   (2006.01)

(52) U.S. Cl. .................. 424/93.21; 435/320.1; 435/325; 435/354

(58) Field of Classification Search .............. 424/93.21; 435/320.1, 325, 354
See application file for complete search history.

(56) References Cited

U.S. PATENT DOCUMENTS

2005/0026169 A1   2/2005   Cargill et al.
2008/0108081 A1   5/2008   Luke et al.

OTHER PUBLICATIONS

Wu, et al.; Molecular Mechanism of Inhibition of Survivin Transcription by the GC-rich Sequence-selective DNA Binding Antitumor Agent, Hedamycin; The Journal of Biological Chemistry, Issue of Mar. 11, 2005, vol. 280, No. 10; pp. 9745-9751.
Ghadersohi, et al.; Prostate-derived Ets transcription factor (PDEF) downregulates survivin expression and inhibits breast cancer cell growth in vitro and xenograft tumor formation in vivo; Breast Cancer Res Treat (2007), vol. 102; pp. 19-30.

*Primary Examiner*—Thaian N Ton
(74) *Attorney, Agent, or Firm*—Hodgson Russ LLP

(57) ABSTRACT

Provided are compositions and methods for identifying agents that can modulate expression of the human survivin gene. The compositions include eukaryotic cells that contain a human survivin promoter sequence operably linked to a reporter gene. The method comprises determining whether a test agent can modulate transcription from a human survivin promoter sequence by adding a test agent to eukaryotic containing a human survivin promoter sequence operably linked to a reporter gene, measuring expression of the reporter gene and comparing expression of the reporter gene from to a control, wherein an increase or decrease of expression of the reporter gene relative to the control is indicative that the test agent can modulate transcription from a human survivin promoter. The method also comprises the use of SPlucTg mice for preclinical drug identification, including testing of candidate drug toxicity and efficacy.

6 Claims, 17 Drawing Sheets

Figure 4A. - SEQ ID NO:1

```
AGATCTGTTCGCCTGACATCCTGTTTGAGCCTGGGTGGAGCAGGACAGCACCTGCCAGCATGGGGAAGCACTCAGATGGGAAGAGGCTTGGTCA
CTCTCCAAAGGTGGCAGGAGTTGGAGGGGGTGAGCTGAAGGTAAGGAGAAAGGAGGTGGGGACCCAGGAGACAGGGGCTGCGCAGCGGGCTC
GGGGCTGACACCCCACGGATACAGTTCASTGGGGNTCAAACATATTGTGGGNGGAAAAGACTTTTYTGCCTTTCTGCCTT
TCTNNTTCTTTCTTTCTTTTTTTTTTTTGAGACAGAGTCTTGTTYATCGCCAGGCTGGAGTGCAGTGGCGTGATCTCGGCT
CACTGCAAGCTCTGCCTCCCGGATCACGCCATTCTCCTGCCTCAGCCTCCCGAGCAGCTGGGACTACAGGCGCCTGCCACCACCCGGSTAT
TTTTTGTATTTTTAGTAGAGATGGGGTTTCACCGTGTTAGCCAGGATGGTCTCGATCTCCTGACCTTGTGATCCGCCCGCCTCGGCCTYCCAAA
GTGCTGGGATTACAGGCGTTGAGCCACCGCAGCCTGGCCAGTGCAGATCCTGCCCCCTTCACTCTTGTTGCCCAGGCTGG
AGTGCAGTGGCGATCCTGGCTCACTGCAACCTCTGCCTCCCAGGTTCAAGCGATTCTCCTGCCTCAGCCTCCTGAGTAGCTGGGACTACAGG
CGCGCACCACCACGCCTGGCTAATTTTGTATTTTAGTAGAGACAGGGTTTCACCATATGTTGGCCAGGCTGGTCTCGAACTCCTGACCTTGATC
TGCCCACCCTCAGCCTCCCAAAGTCCTGGGATTACAGGCGTGAGCCACCGTGCCCAGCCTAATTGTCCAGTGAATGCTATGCAAATATTTCATG
TCACAGCCTTCTCTGTCATTATAAGTCCACACTGATCTCGGGGTTGCAGATGCCCCAGGCTGGGATCCCCCACCCTTCATCCACCTTGGTACCTTC
GATATGTACTTGGTACGCACTGATCTCGGGGTTGCAGATGCCCCAGGCTGGGATCCCCCACCCTTCATCCACCTTGGTACCTTC
AGATGTGCCAGTGGGCCCAGGCACTCAAGTTATGCGTCTAGACATGCGGATATATTCAAGCTGGGCACACAGCAGCCCACTGCTTCCCCCGTCTTTCTCAGC
CGTGACTCCTGCCTTCAGGCACTCAAGTTATGCGTCTAGACATGCGGATATATTCAAGCTGGGCACACAGCAGCCCACTGCTTCCCCCGTCTTTCTCAGC
GAAATCAGAGCTGGGTCCAAAGGACCACACACCCGAGGACTGTGTGGGAGCTGGCACTTTGTAGAAGCCCCTTGAAGCTTTTGAAGCTCCTAACTTACAC
CATTCCTGAAGTCAGCCTCACTCTGCTTCTCAGGGATTTCAAATGTCAGAGACTCTGGACATTTGATGACATTGTGTGCAAGAGTCAAATACCAGCTGACGAGCTTTGAGCAACTCGGTT
CTGATGCTGTGCGGCTCGTCTCCGGGGAGGCTGTTCCTTGTCCTTGAGGAGGCTGGAGGCTGGGGCATGGTGCCCACTGCTGTAATCCCAGCTACTTTGGGGAGTCAATGTGGGA
TGAGGGTGTTCAGGTGCAGGTGCCTTCTACTAAATTACAAAATCCGGACCAAGAGTTGCAGTGAGCCGAGATTGCGCCACTGTATTCCAGCCTGGGCAACAAGAGCAGAGACTCTGTCTCAAAAA
AACCCCGTCTCTACTAAATACAAAAATTAGCCGGGCATGGTGGCGGGCGCCTGTAATCCCAGCTACTCGGGAGGCTGAGGCAGGAGAATCGCTTGAACCCGTGGCGGGGAGG
AACAAAAAAAAAGTGAAAAGGAGTTGTTCCTTGTCCTCTGAGGGCAGCAGCAATCAGCGAGCCAATCAGGAGCCAATCAGCGAGCCAATCAGGGTTAGCGCAGGAGAATCGCTTGAACCCGTGGCGGGGAGG
ATACAAAAAAAAAGTGAAAAGGAGTTGTTCCTTGTCCTCTGAGGGCAGCAGCAATCAGCGAGCCAATCAGGAGCCAATCAGCGAGCCAATCAGGGTTAGCGCAGGAGAATCGCTTGAACCCGTGGCGGGGAGG
AGGTTGCAGTGAGCCGAGATCATGCCACTGCACTCCAGCCTGGGCGACAGAGCGAGACTCCGTCTCAAAATAAATAAATAAAAACCCAAAATGAAAAGACAGTG
TACTGTATTAAGAATGGGGCCCTGCGTGGGCTGAGGAGAAGGTTCCAAGAGCTAATAAGCAGCTAATAATAAACCCAAAATGAAAAGACAGTG
GAGGCACCAGGCCTGCGTGGGCTGAGGAGAAGGTTCCAAGAGCTAATAAGCAGCCAGGAGGACACCCCTGGAAGGCCGGGGTCCGAAGAAGTTGATGATGCCCA
GCTCCAGAGTGACTCCAGAACACCCTGTTCCAAAGGAGAGTTGCCCTGACTCGTTCAAGAACGCAGCCCCCTGATTTTTTTTCACTGGGCTTTCCACTGGGCTTTCCACTGGGCTTGCACCAAGTGATGTCACGTGTAGT
TGCTTTGCGAAGGGAGTTTTGCCCTGACTGCTCAGAAGGTTGCCCTGAAACCCAGGTGCAGCCGGTCGCAGGATGGATCACAGTTGTGGCACGTGAAGCTCCTGTCTGACT
TTTTTTTTTTAGACTGAGTTTTGCTCTTGTTGCCTCAGGTAGTTGGATTACAGCCATGCCAATGGCAACATCTCAGCTGCCCTCCACCCTCGCCCTCGCACCCTCGCACCCTGAAAGCTCGTAATTTTTAGTAGAGACAAGGTTTCAC
CGTATGACCAAGCTGGTCTTGAACCAAGCCTGGGATCCGCTCAGGGTACAGCAGTCAGTCACCGCCTCAGCCGGCGCCCTCCCCGCGCGGCCTCCCCGCGCCCCCCGCGCCCCCCGCGCCCCCCGCGCCCCCCGCGCCCCCCGCGCCCC
CGGCCTGGCACGCGCGTCTTTGAAAGCAGTGAGGGGCGCGCGTAGGTTGCGAGGCGCCCAGATTTGAATCGCGGGCGCCATTAACGCGGGGCGCGCACCGGGCGCGGGCGCAGCAGAAGGCCGCCGCGCACCGGGGCGCGCGCGCGCGCGCGCGCGCGCG
GGCAGAGCATGCCCCGGGGGCGCGCGCACCGGCGCGCGCGCGCGCGCGCGCGCGCGCGCGCGCGCGCGCGCGCGCGCGCGCGCGCGCGCGCGCGCGCGCGCGCGCGCGCGCGCG
GAGGGGCTCCCGGACATGCCCCGGGCGCGCGCACCGGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCGCG
```

GGCA+1 (4081 bp)

Figure 4B. - SEQ ID NO:9

```
AGATCTGTTGCCTGACATCCTGTTTGAGCCTGGGTGGACAGGACAGCACCTGCCAGCATCGGGAAGCACTGCAGATGGGAAGAGGCTTGGTCA
CTCTCCAAAGTGGCAGGAGTTGGAGGGGTGAGCTGAAGGTAAGGAGAAGGAGGTGGGAACCCAGGAGACAGGGGCTGCGCAGCGGGCTC
GGGGCTGACACCCCACGGATACAGTTCASTGGGGNTCAAACATAAAGGAACCAACTATTGTGGGNGGAAAAGACTTTYTGCCTTTCTGCCTT
TCTNNTTTCTTTTCTTTCTTTTTTTTTTTTGAGACAGAGTCTTTGTTYATCGCCCAGGCTGGAGTGCAGTGGCGTGATCTCGGCT
CACTGCAAGCTCTGCCTCCCGGGATCACGCCATTCTCCTGCCTCAACCTCCCGAGCAGCTGGGACTACAGGCGCCTGCCACCACACCGGSTAT
TTTTTGTATTTTTAGTAGAGATGGGGTTTCACCGTGTTAGCCAGGACGGTCTCGATCTCCTGACCTTGTGATCCGAGACAGAGTTTCACTCTTGTTGCCCAGGCTGG
GTGCTGGGATTACAGGCGTGAGCCACCGCGCCTGGCTCATTCTGCCAACCTCCACCTNCAGGGTCTCCACTCCAGCCTCTGCAAGTGGGGACTCAGG
AGTGCAGTGCCGCGATCTTGGCCTCACTGCAACTCCACCTNCAGGGTTCACCATATTTGTATTTTAGTAGAGACAGGGTTTCACCATGTTGGCCAGGCTGGTCTCGAACCTGACCTTGATC
CGCGCACCACCACCCAGCCTGCCCAAAGTCCTGGAGTTACACCGGCGTGAGCCTAATTTGTCCAGTGAATGTATGCAAATATTTCATGCACCTGCTGATCGCAGGAAT
TCACAGCCTCTCTTGTCATATAAGTCACACTGATCGTCACCACCGGCTGGCCCAGGCTGTGGGAAGAGAGGGCAAGAGAGGAATAGCCCCTCCTTCCTGGTCACCTTC
GATATGTACCTTGGTACGGGGCCCAGGCTGCGTGCAGATGGGCCCCTCCCAGAGACATATTCAAGCTGGGCACACACAGGCCACACACGCACTGCTTCCCCCGTCTTTTCTCAGC
GATGTGCCGATGGGGCCCAGGCTGCTCAGTTATGCGTCTAGACATGCGGGCTCGGGGCAGAGCTGGTGGGGACACCTTTTCAATGCAGGGGCACACACAGGCAGCTT
GAAATCAGAGCTGGGGTCAAAGGAACCACACACCTCAGGATTCAAATGCAGAGACTCTGGGATCACATTTGATGACATTTGTGCAGAAGTGAAAAGAGCTTTTGAAGCCTGAACTCGGTTT
CATTCCTGAAGTCAGCTCACTCTGTCAGGTGGACACCTCTGGGCTGTCTCCTTGTCCATGCATTTGATGACATCACGAGGTCAATAACCAGCTCAGCTTTGAAGCCCTGAACTCGGTTT
CTGGATGCTGTCAGGTGCCTGTAATCCCAGCACTTTGGGAGGCTGAGGCATGGTGGCGGGCGCACTGTGTGCCACTGCACTGCTGGGACAGGCAGCAACTCGGGACAGTGGAGGTTGCCAGTGAGCCGAGATCGCGCCACTGCACTCCAGCCTGGGCAACAAGAGCGAGACT
TGAGGGTGTTCAGGTGCCTATGCGTGTAATCCCAGCACTTTGGGAGGCTGTGGGAGGCGGGCCACTGTGTGGCGGGCGCATGTGCCACTGCACTGCTGGGACAGGCAGCAACTCGGGACAGTGGAGGTTGCCAGTGAGCCGAGATCGCGCCACTGCACTCCAGCCTGGGACAAGAGCAAGACT
TGAGGGTGCTCCCTGGCTTATGCCTGTAATCCCAGCACTTTGGGAGGCTGAGGCTGGCAACCTGAGGTCAGGAGAGTTCAAGACCAGCCTGGCCCAGGTGGCGCCAAGATGGTGAAACCCGTGGCTCACATCTCTACTAAAA
ACTCCCGGGAGGTTAAAAATTAGCCTGGTGTGTGTAAAGCATGTAAAAACCACCAACACCTGTGTCTCTACTAAAAATACAAAAATTAGCCGGGCGTGGTGGTGGGCGCCTGTAATCCCAGCTACTCGGGAGGCTGAGGCAGGAGAATCGCTTGAACCCGGGAGG
CAAACCGGGAAGGGGTAAGAGAGGGAGAGAGAGTAGGTTGGGAGAAAGTAGGTTGCAGAGGGAGAGGAGCAGAGAAGTGAATGTTAAAGGAAACAGGCAAACATAAACAGAAAA
TCTGGGTGAAGGTATATGAGTATTCTTGCAATTATCTTGAGGTCAGGAGTTTGAGACCAGCTGAGACTCAGTTCAAAATAATAAATAATTTAAAGGAAACAGGCAAACATAAACAGAAAA
CCCAGCACTTTGGGAGGCCGAGGCAGGCAGATCATGCCACTGCACTCCAGCCTGGGCGACAGAGCGAGACTCAGTTCAAAATAATAAATAATTTAAAGGAAACAGGCAAACATAAACAGAAAA
ATACAAAAATTAGCCAGCAGGCAGATCATGCCACTGCACTCCAGCCTGGGCGACAGAGCGAGACTCAGTCTCCAAAATAATAAATAAACCCAAATGAAAAGACAGTG
AGGTTGCAGTGAGCCGAGATCGGGCGCCACTGCACTCCAGCCTGGGAGAGGTGCAAAAATAAATAAACCCAAATAAATAAAACAGCCTTCAAATAATAAATAACCCAAATGAAAAGACAGTG
TACTGTATTAAAGAATGAATGAGCCGGGCAGGGTGAGGCGAGGCAGGCAGGCTAATAAGGCAGAGGTTGGGCCAGGCCTGGAGGCCTAATAAGGCAGAGGTTGGGCCAGGCCTCTTATCTCTGCCATATAGAACCAGAGAAGTGAGTGATGTGATGCCA
GAGGCCAGCAGTGACTGCTGCGTGGGCTGGGGCTGTAATAAGGCAGAGGTTGGGCCAGGCCTCTTATCTCTGCCATATAGAACCAGAGAAGTGAGTGATGTGATGCCA
GCTCCAGAAGTGACTCCAGAAGAGGGAAGAGGAGTTGCCCTGCCCAAAGCAAGACAGAAGCACACTGCATTTTTTTTAATAGGCTGCAGGACTTACTGTTGGTGGGACGCCC
TGCTTTGCGAAGGAAAGGGAAAGGGAGTTGCCCTGCCCAAAGCAAGACAGAAGCACACTGCATTTTTTTTAATAGGCTGCAGGACTTCCTTGTCTTGTCTTTATCACGGTAGT
GGCCAGTCCCTGGCCCTCGACTCAGTCCAGAAGGTTGCCCTCCTGAAAACCCAGGTCCTGCAAGCCAGTTACTGCCAGTCAACAGTACTGCCGTCAACGTGTCTGC
TGCACTCCATCCCTCCCTGTTCATTTGTCTCTTGTGCCTGGATTACAGGCGGGGAGACTCAAGGGTCATCGCAATTCAGCTCTCAAAGTGTTGGATTACAGGCGTGAGCCACTGCACC
TTTTCTCTGCCTCAGTGAGTTTGCTCTTGTGCCTGGATTACAGGCGGGGAGACTCAAGGGTCATCGCAATTCAGCTCTCAAAGTGTTGGATTACAGGCGTGAGCCACTGCACC
CGATGATGGCCACGCGTTCTTGAAAAGTAGTGCAGTGAGGTGTGGGGACGAGTGCGCGCCCCCGCGCCCTCGCTGGGTGCGCCGACCACG
CGCCTGCACGCGTTCTTGAAAAGTAGTGCAGTGAGGTGTGGGGACGAGTGCGCGCCCCCGCGCCCTCGCTGGGTGCGCCGACCACG
GGCGAGCACGCATGCCGGAGGACTACAACTCCCCGGGGGGCCCCGGGCGGCCCGGGACACTGCCCCGCGGCTCTACTCCCGAGAAGGCCGTGGACCGGCTAA
GGGCGAGCACGCATGCCGGAGGACTACAACTCCCCGGGGGGCCCCGGGCGGCCCGGGACACTGCCCCGCGGCTCTACTCCCGAGAAGGCCGTGGACCGGCTAA
GAGGGCGTTGCCGCTCCCGACATGCCCCGCGGCTCTACTCCCGAGAAGGCCGTGGACCGGCTAA
```

GATTT-39 (4042 bp)

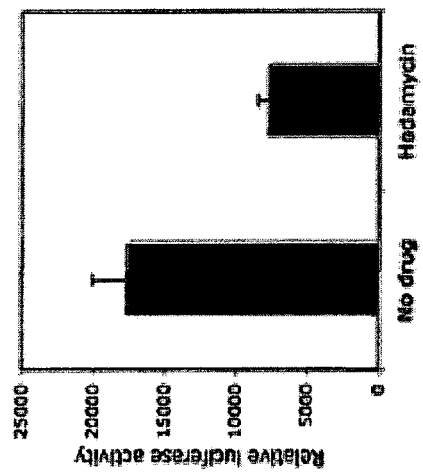
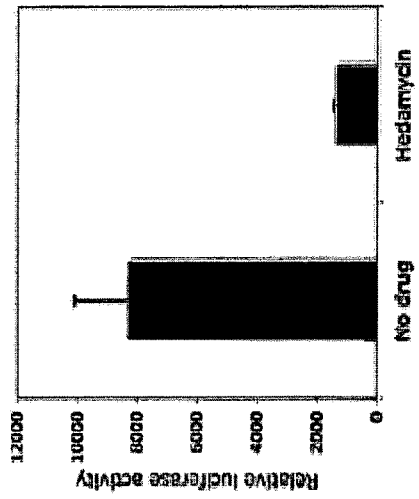
Fig. 5 A549 lung cancer cells transfected with pNeoHScyc4.08-luc
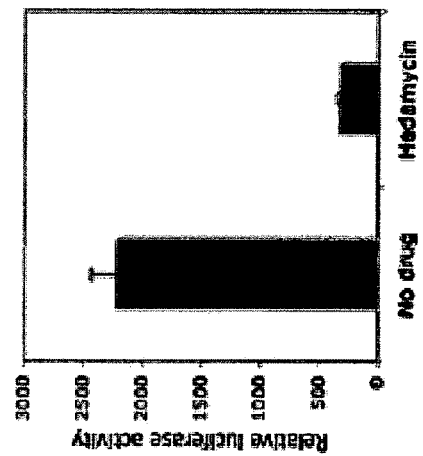
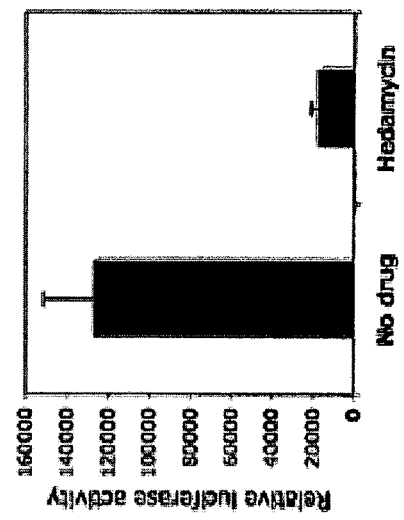
Fig. 6 2008 ovarian cancer cells transfected with pNeoHScyc4.08-luc

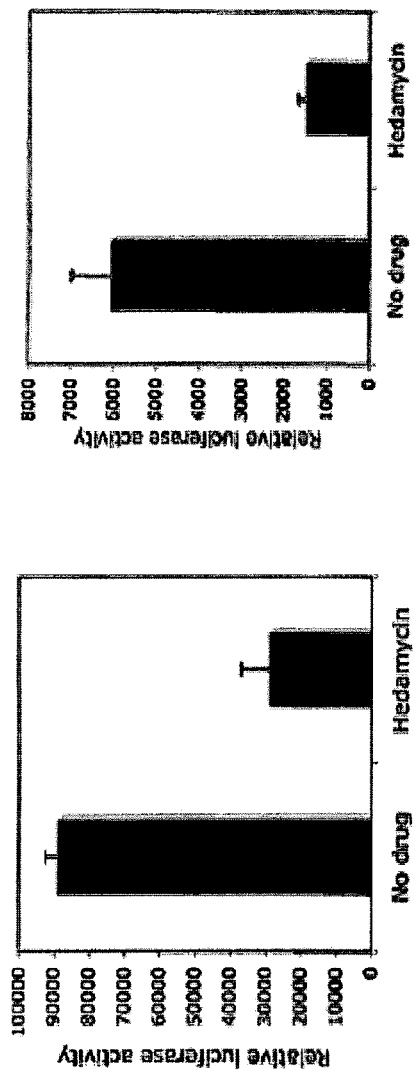
Fig. 7. HCT116 colon cancer cells transfected with pNeoHScyc4.08-luc
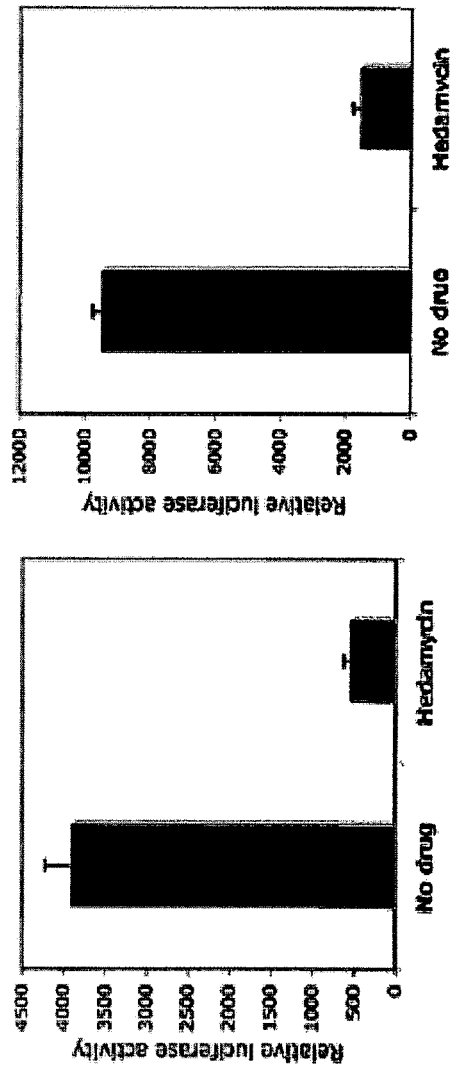
Fig. 8. PC-3 prostate cancer cells transfected with pNeoHScyc4.08-luc

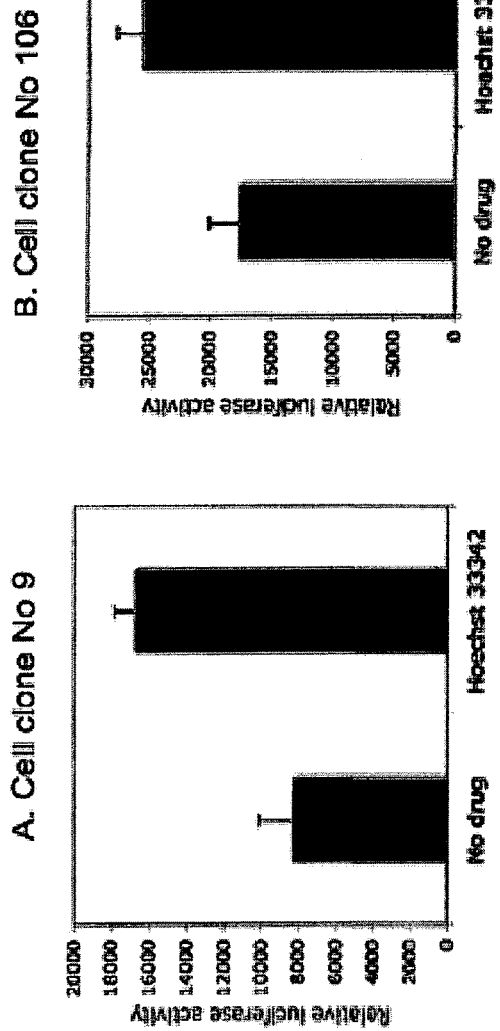
Fig. 9 A549 lung cancer cells transfected with pNeoHScyc4.08-luc
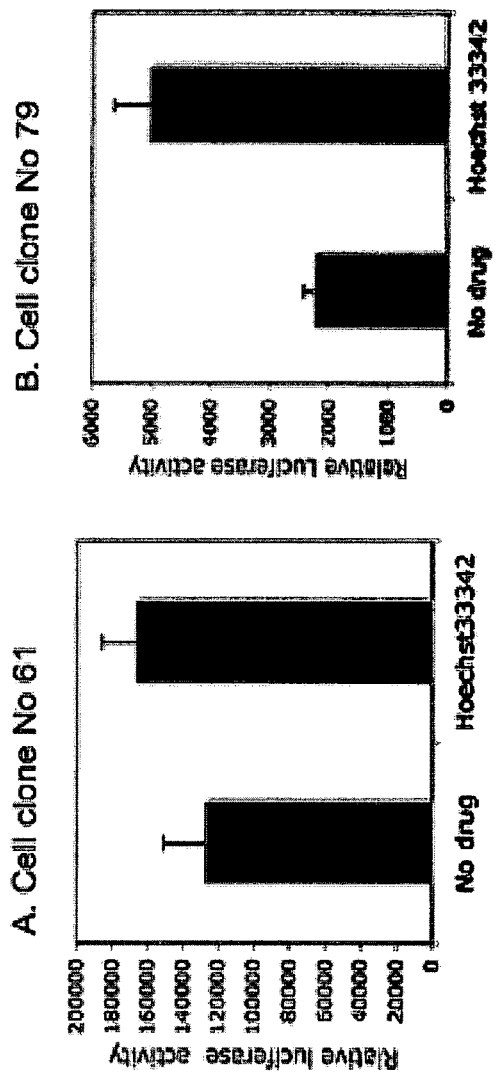
Fig. 10. 2008 ovarian cancer cells transfected with pNeoHScyc4.08-luc

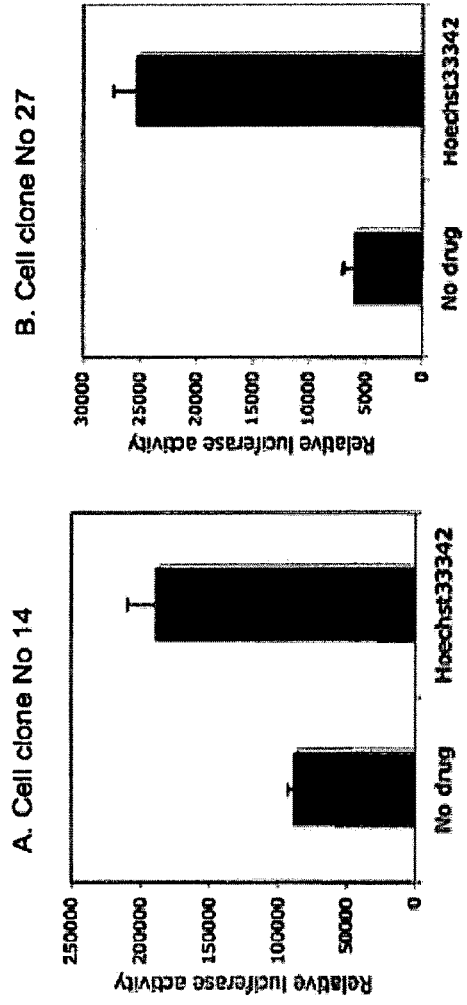
Fig. 11. HCT116 colon cancer cells transfected with pNeoHScyc4.08-luc
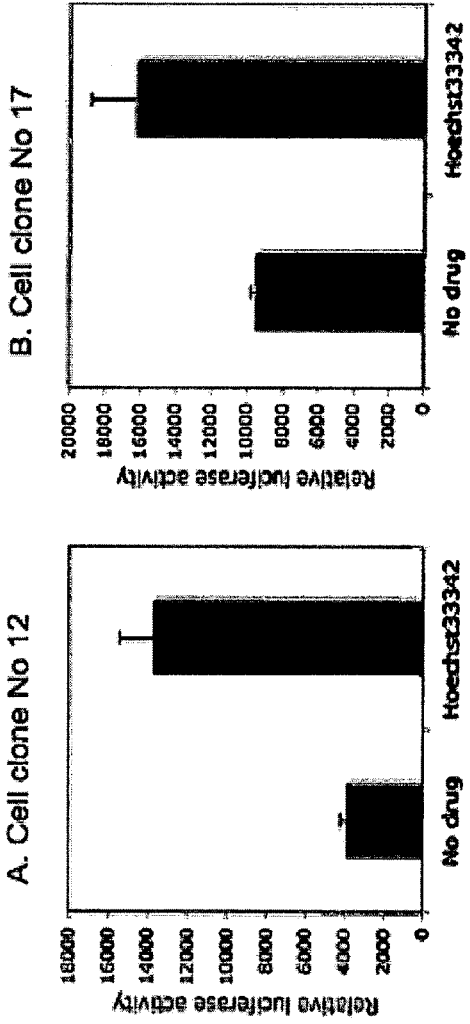
Fig. 12. PC-3 prostate cancer cells transfected with pNeoHScyc4.08-luc

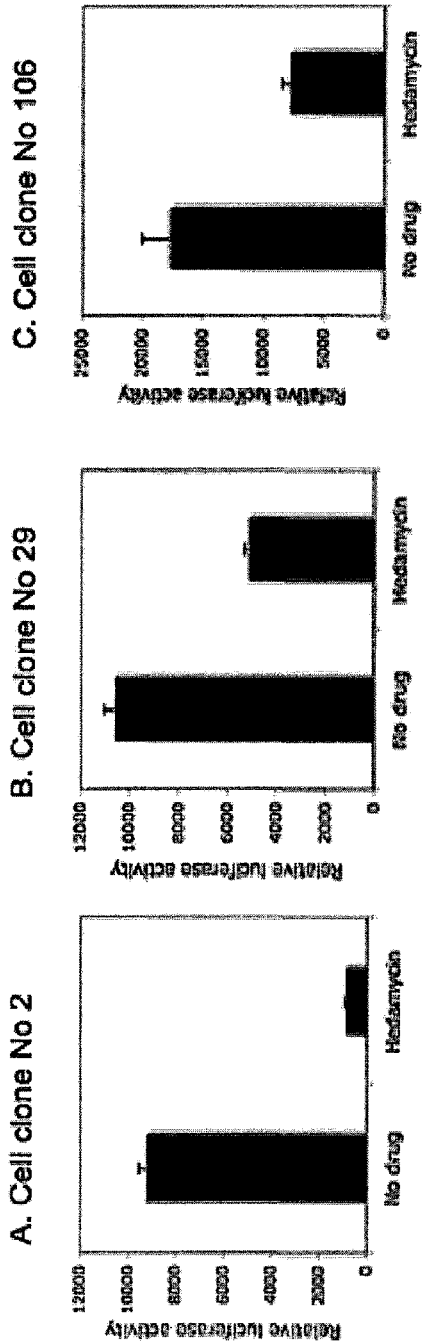
Fig. 13. A549 lung cancer cell clones transfected with pNeoHS4.04-luc
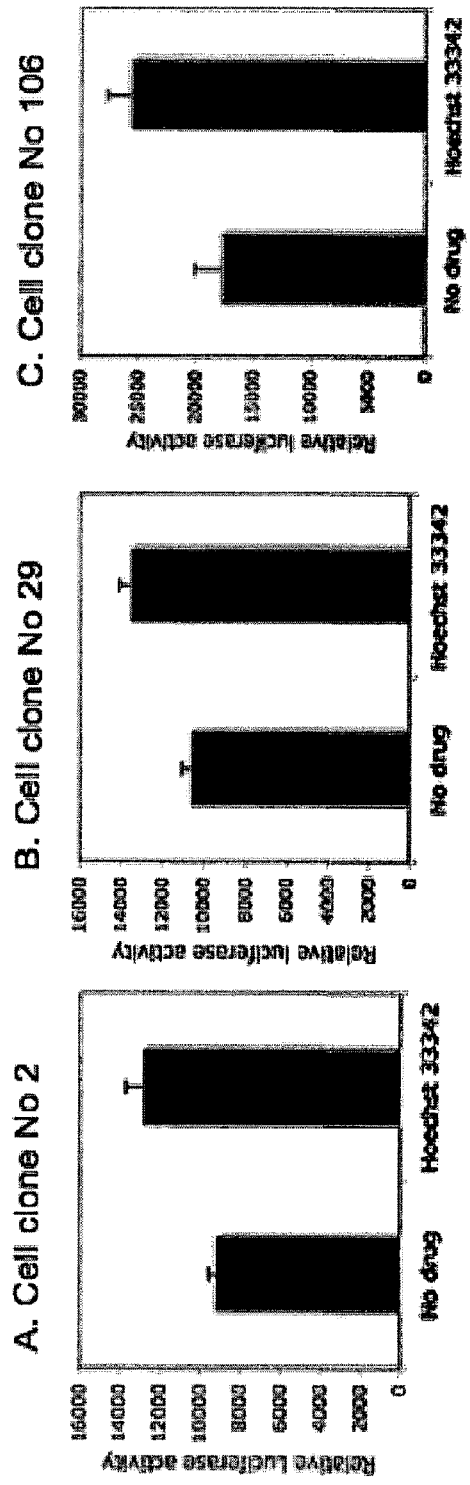
Fig. 14. A549 lung cancer cell clones transfected with pNeoHS4.04-luc

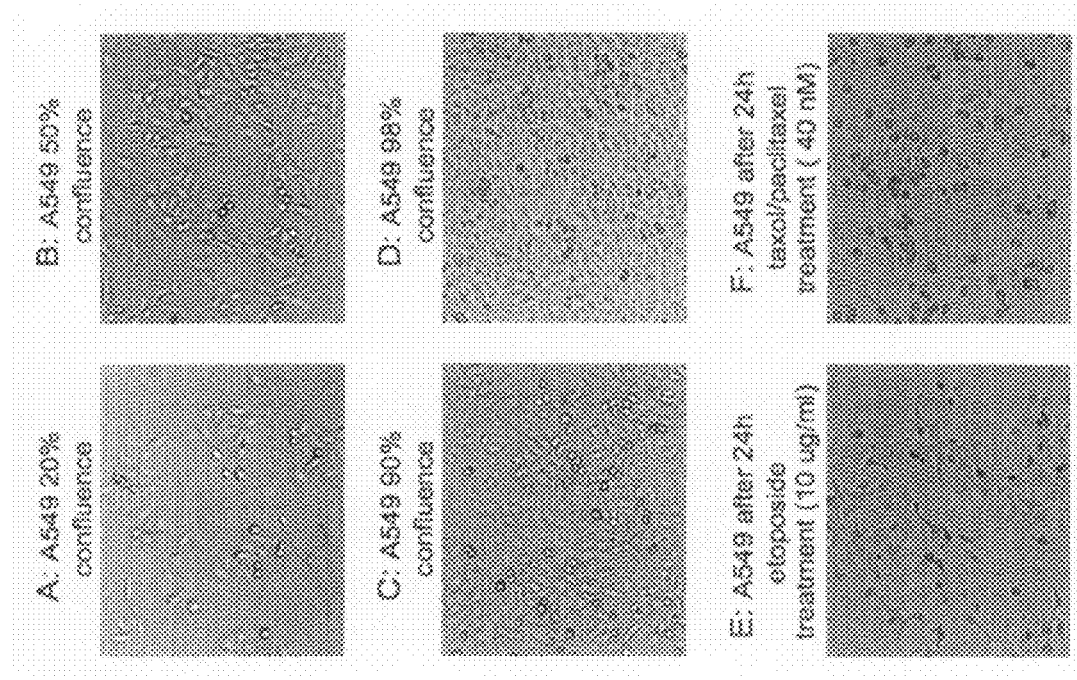
Fig. 16. A549 model cell morphology in various confluence or drug treatments as shown.

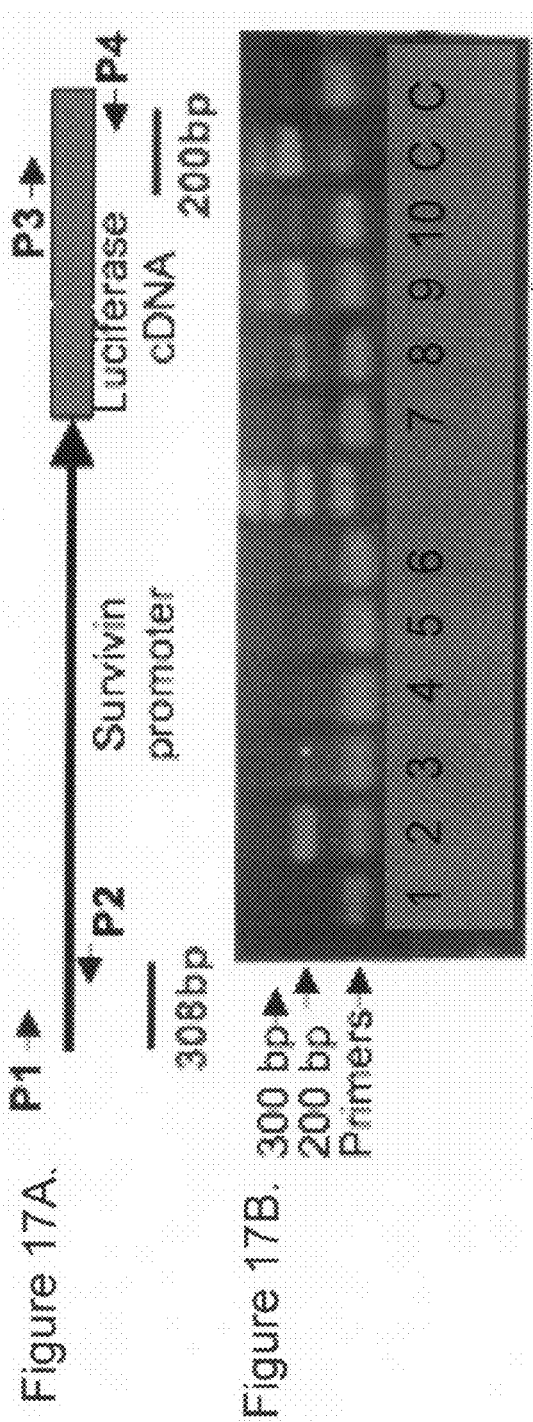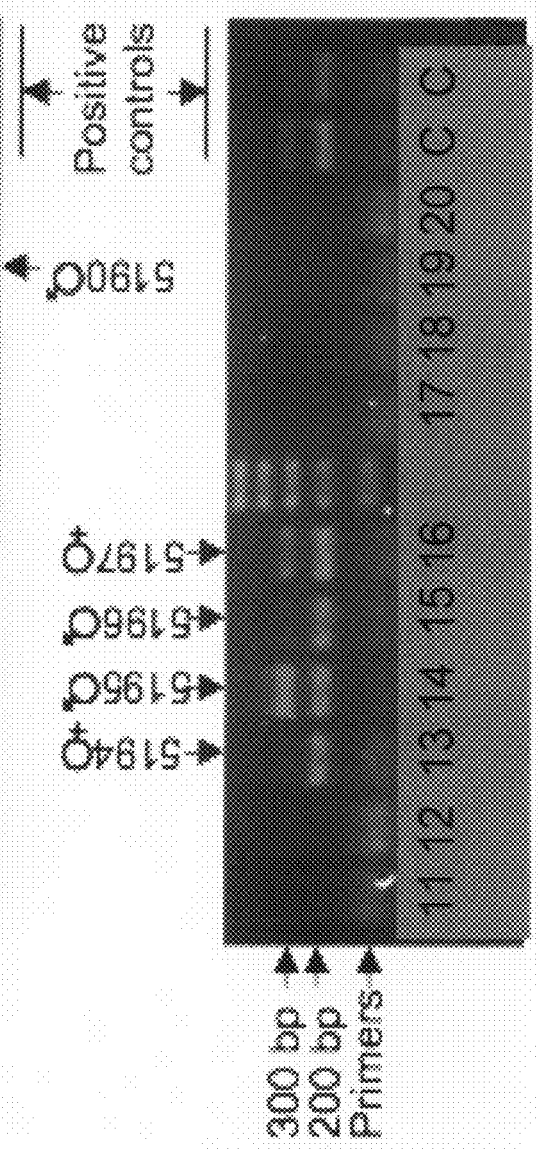
Figure 17A.
Figure 17B.

COMPOSITIONS AND METHODS FOR IDENTIFYING AGENTS THAT ALTER EXPRESSION OF SURVIVIN

This application claims priority to U.S. provisional patent application Ser. No. 60/865,254, filed on Nov. 10, 2006, the disclosure of which is incorporated herein in its entirety.

FIELD OF THE INVENTION

The present invention relates generally to tools for identifying drug candidates and more specifically to compositions and methods for identifying agents that can modulate expression of the human survivin gene.

BACKGROUND OF THE INVENTION

Survivin is a novel member of the inhibitor of apoptosis (IAP) protein family (1, 2). Different from other IAP members, survivin expression is undetectable in normal, differentiated adult tissues but is highly expressed in all common human cancers (1). Many important gene products including kinase and phosphatase molecules, transcription factors and other ligands or signaling molecules appear to exert their functions in various human pathological conditions (3) including cancer (2, 4), through the modulation of survivin expression (5). Survivin expression has been shown to be associated with tumorigenesis (4), cancer progression, poor disease outcome, shorter patient survival and drug/radiation resistance (1, 2). More importantly, survivin also appears to be required for angiogenesis, e.g. endothelial cell proliferation and migration (1). Thus, inhibition of survivin will not only directly induce apoptosis but also will block angiogenesis during tumor progression. Intriguingly, the gene regulation and the functional mechanism for survivin in cancer appear to be different from that in the rare survivin-positive normal tissues or cells (3, 5). Thus, targeting survivin for cancer therapeutics would produce minimal toxicity to normal human tissues and organs. These observations make survivin not only an exciting novel molecular target for cancer treatment but also a universal biomarker and target for drug discovery and development.

While survivin is a validated ideal target for cancer treatment, survivin is also, however, a multifunctional molecule with multiple unique subcellular localizations. For example, survivin has been shown to associate with both mitotic spindles (6) and centromeres (7, 8) during mitosis (1) as well as on mitochondria (9). Its expression is involved in both the inhibition of apoptosis (6, 9) and the regulation of mitotic cell division (7, 8, 10, 11). Moreover, recent studies on survivin reveal emerging new roles for survivin in the promotion of $G_1$/S transition (3) and the regulation of gene transcription (5). For example, survivin plays a critical role in the mediation of vitamin D3 (VD3) compound-induced cancer cell growth inhibition ($G_0$/$G_1$ arrest) and apoptosis induction (12). Therefore, the multiple functions and subcellular localizations of survivin raise concerns as to whether it will be possible to find a tractable and effective way to inhibit its multiple functions for cancer treatment. Thus, there is an ongoing need to develop tools for identifying agents that can affect survivin expression.

SUMMARY OF THE INVENTION

The present invention provides eukaryotic cells comprising a human survivin promoter polynucleotide sequence operably linked to a reporter gene. The cells are useful for identifying agents that can modulate survivin gene transcription. In one embodiment, the cells are stably transfected cancer cells lines. In another embodiment, the invention provides a transgenic mouse comprising a germ line insertion of the survivin promoter in operable linkage with the reporter gene.

Also provided are methods for identifying agents that can modulate survivin expression. The method comprises adding a test agent to cells comprising a human survivin promoter in operable linkage with a reporter gene. By comparison with a control, agents that can either increase or decrease transcription from the survivin promoter, as evidenced by increased or decreased expression of the reporter gene, can be identified. Thus, the invention is suitable for identifying agents that are expected to have therapeutic benefit for cancer patients, as well as for other disorders wherein it would be desirable to modulate the expression of survivin.

BRIEF DESCRIPTION OF THE FIGURES

FIG. 4A presents the 4.08 Kb survivin promoter sequence (SEQ ID NO:1); FIG. 4B provides the 4.04 Kb sequence (SEQ ID NO:9).

FIG. 5 provides a graphical depiction of the effect of hedamycin on A549 lung cancer cells (different expanded clones are shown in panels A and B) transfected with pNeoHScyc4.08-luc.

FIG. 6 provides a graphical depiction of the effect of hedamycin on 2008 ovarian cancer cells (different expanded clones in panels A and B) transfected with pNeoHScyc4.08-luc.

FIG. 7 provides a graphical depiction of the effect of hedamycin on HCT116 colon cancer cells (different expanded clones in panels A and B) transfected with pNeoHScyc4.08-luc.

FIG. 8 provides a graphical depiction of the effect of hedamycin on HCT116 PC-3 prostate cancer cells (different expanded clones in panels A and B) transfected with pNeoHScyc4.08-luc.

FIG. 9 provides a graphical depiction of the effect of Hoechst 33342 on A549 lung cancer cells (different expanded clones in panels A and B) transfected with pNeoHScyc4.08-luc.

FIG. 10 provides a graphical depiction of the effect of Hoechst 33342 on 2008 ovarian cancer cells (different expanded clones in panels A and B) transfected with pNeoHScyc4.08-luc.

FIG. 11 provides a graphical depiction of the effect of Hoechst 33342 on HCT116 colon cancer cells (different expanded clones in panels A and B) transfected with pNeoHScyc4.08-luc.

FIG. 12 provides a graphical depiction of the effect of Hoechst 33342 on PC-3 prostate cancer cells (different expanded clones in panels A and B) transfected with pNeoHScyc4.08-luc.

FIG. 13 provides a graphical depiction of the effect of Hedamycin on A549 lung cancer cells (different expanded clones in panels A, B and C) transfected with pNeoHScyc4.04-luc.

FIG. 14 provides a graphical depiction of the effect of Hoechst 3342 on A549 lung cancer cells (different expanded clones in panels A, B and C) transfected with pNeoHScyc4.04-luc.

FIG. 16 provides a photographic representation of microscopic analysis of A548 cells in various confluence or drug treatments.

FIG. 17 provides a photographic representation of the identification of the transgene cassette by PCR amplification. FIG. 17A depicts the PCR strategy used to identify both the human survivin gene promoter and the luciferase gene sequence. FIG. 17B depicts electrophoretic separation of PCR products demonstrating the presence of the construct in SPlucTg founder mice separated.

DESCRIPTION OF THE INVENTION

Figure 1:
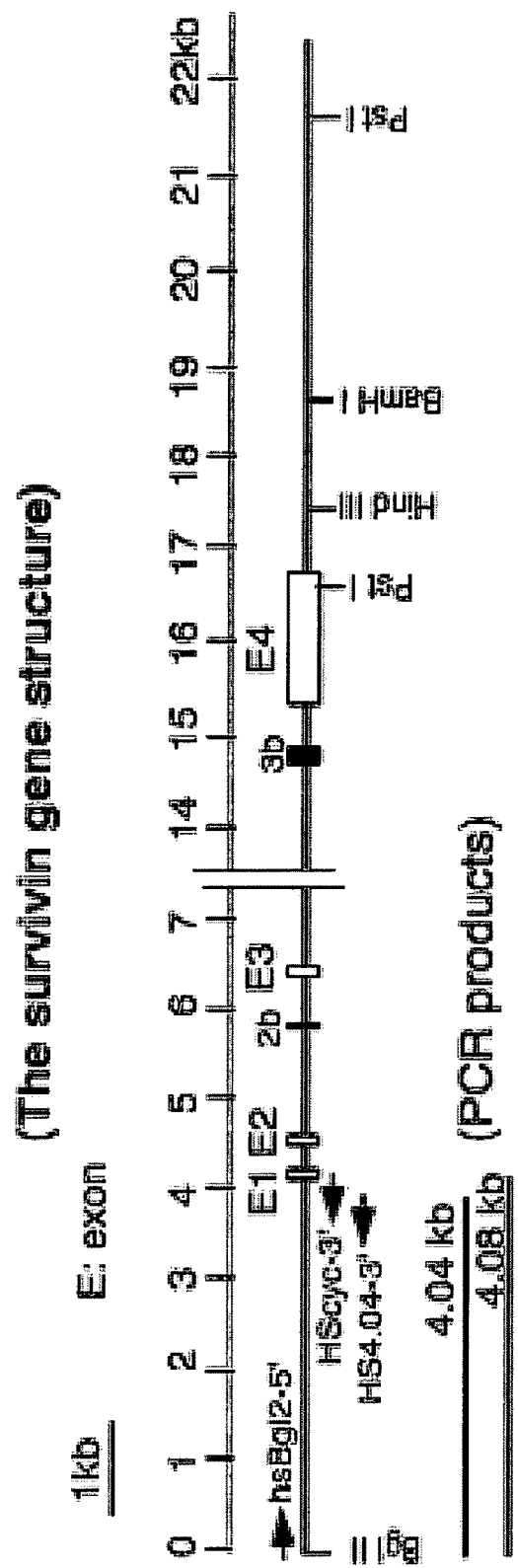
FIG. 1 provides a diagram of the survivin gene structure and primers used for polymerase chain reaction (PCR) and the corresponding products amplified. There are 4 dominant (E1, E2, E3 and E4) and 2 hidden (2b and 3b) exons for the survivin gene. E1, exon 1; E2, exon 2; 2b, exon 2b; E3, exon 3; 3b, exon 3b; E4, exon 4.

The present invention provides eukaryotic cells containing a human survivin promoter DNA sequence wherein the survivin promoter sequence is operably linked to an exogenous reporter gene. By "operably linked" it is meant that the survivin promoter sequence and the reporter gene are present in a contiguous polynucleotide, and that the promoter sequence is capable of recruiting transcription factors so as to drive transcription of the reporter gene. The DNA sequence comprising the survivin promoter sequence and the reporter gene is present in the cells as a stably transfected vector, or as an integrated transgene construct, such as in a chimeric or transgenic animal. Thus, the invention provides both in vitro and in vivo systems useful for testing agents for the capability of modulating transcription from the human survivin promoter. The in vivo systems enables analysis of various pathophysiological conditions, including tumor initiation, progression and metastasis.

In one embodiment, the eukaryotic cells of the invention contain a DNA polynucleotide comprising a 4.08-kb human survivin promoter DNA sequence operably linked to a reporter gene. The 4.08 kb sequence is provided as SEQ ID NO:1 and in presented in FIG. 4A.

In another embodiment, the cells comprises a 4.04-kb human survivin promoter sequence operably linked to a reporter gene. The 4.04-kb survivin promoter sequence is identical to SEQ ID NO:1, but lacks nucleotides −1 to −38. The 4.04-kb sequence is presented as SEQ ID NO:9 (FIG. 4B).

In another embodiment, the invention provides a method for identifying agents that can modulate transcription driven from the human survivin promoter. The method comprises adding a test agent to a plurality of cells comprising a human survivin promoter in operable linkage with an exogenous reporter gene and comparing expression of the reporter gene with a control. The control may be cells comprising the human survivin promoter in operable linkage with the reporter gene, but to which the test agent is not added, or to which an agent with a known effect on the survivin promoter is added. Alternatively, the control can be a predetermined value, such as a standardized curve. Thus, by comparison with the control, agents that can modulate (i.e., either increase or decrease) transcription from the survivin promoter can be identified by measuring alterations in expression of the reporter gene. It will be recognized by those skilled in the art that an agent identified according to the present invention as being capable of modulating transcription from the human survivin promoter would be expected to be able to elicit a similar effect on endogenous survivin gene expression when administered to a human.

In one embodiment, cells comprising the human survivin promoter sequence in operable linkage with an exogenous reporter gene are stably transfected cancer cells lines. By "stably transfected" it is meant that the DNA polynucleotide encoding the survivin promoter sequence in operable linkage with the exogenous reporter gene can be maintained over at least several passages of the cells in the absence of a selection agent, or over an essentially unlimited passages of the cells in the presence of a selection agent. Accordingly, the polynucleotide comprising the survivin promoter and reporter gene may also comprise a selectable marker to maintain the presence of the construct in the. The selectable marker may be any selectable marker as will be known to those skilled in the art.

In one embodiment, the selectable marker encodes for neomycin resistance and can thus be employed in the well known G418 selection process. Other selection markers may be used including, but may not be limited to, hygromycin, Thymidine kinase (TK). Additionally, any reporter gene may be used in the invention. For example, suitable reporter genes include but are not limited to luciferase (e.g., firefly or Renilla), green fluorescent protein (GFP), enhanced GFP (EGFP), β-galactosidase, alkaline phosphatase and chloramphenicol acetyl transferase. In one embodiment, firefly luciferase is used as the exogenous reporter gene.

In another embodiment, cells containing a polynucleotide comprising the survivin promoter in operable linkage with an exogenous reporter gene may be administrated into an animal. For example, the cells with a recombinant expression vector may be administered to an animal for the expression of the reporter gene via the operably linked human survivin promoter. Alternatively, the animal may be a transgenic animal, such as a transgenic mouse, wherein each nucleated cell in the animal contains a chromosomally integrated polynucleotide sequence comprising the survivin promoter and the exogenous reporter gene. Techniques for creating transgenic animals, and particularly for creating transgenic mice, are well known in the art. Also, techniques for measuring expression of a reporter gene in vitro and in vivo are known.

In one embodiment, expression of a reporter gene driven from a human survivin promoter sequence in a whole animal can be measured. For example, expression of luciferase can be visualized using the commercially available XENOGEN IVIS® in vivo Imaging System. Alternatively, conventional immunoblotting/Western blots or immunohistochemical techniques or other assays performed on biological samples obtained from the animal may be used to detect and quantify modulation of expression of the reporter gene in response to the test agent and compared to a control.

Figure 15:
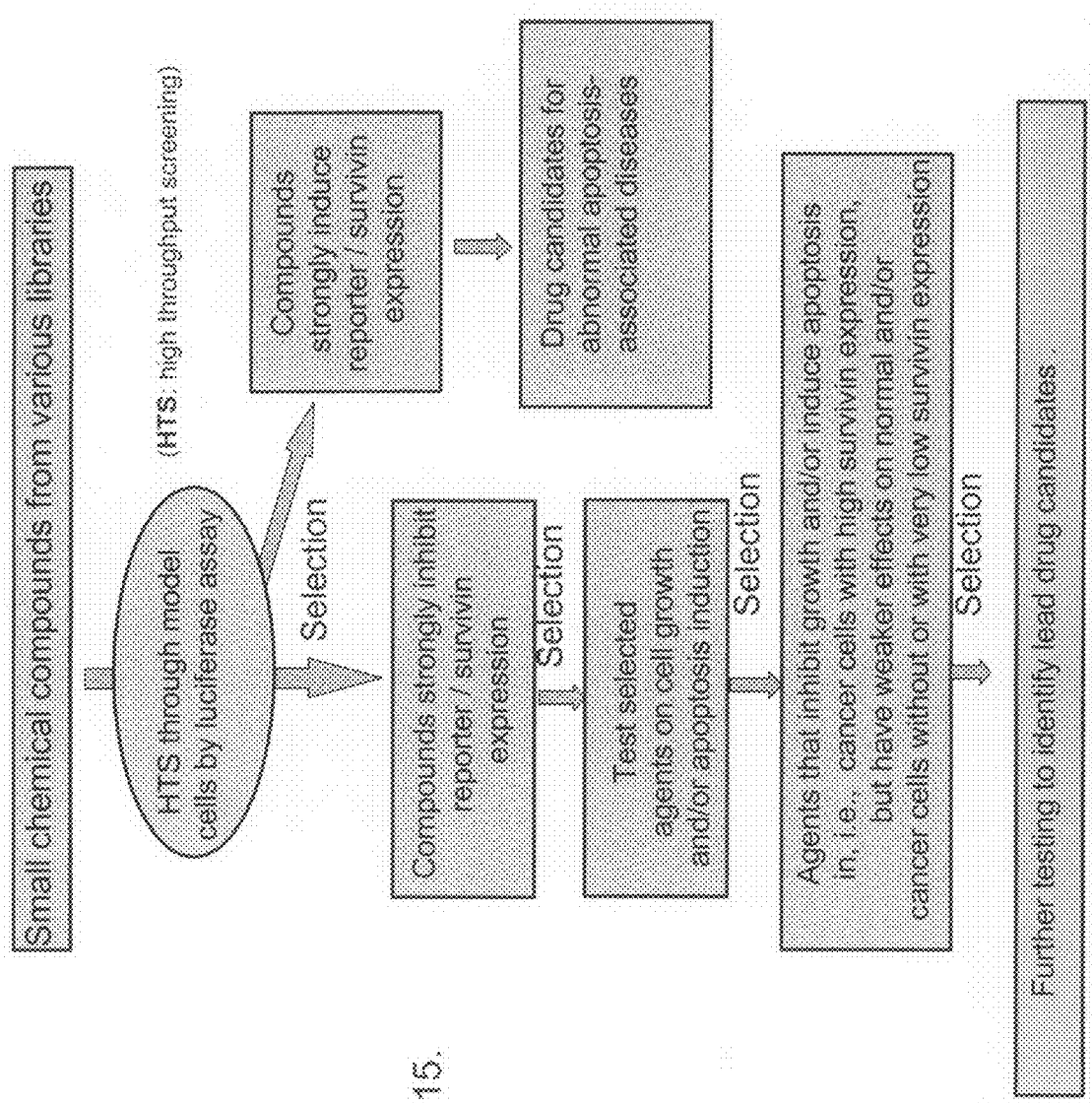
FIG. 15 provides a flow-chart depicting the steps of drug discovery according to the present invention.

Thus, and without intending to be bound by any particular theory, we believe that control of survivin transcription is an important and tractable approach to ablate the multiple functions of survivin in cancer cells and to boost its expression for enhancing normal cell survival in certain apoptosis-associated pathological situations such as neurodegenerative diseases. An additional advantage of this strategy is that the regulation of survivin expression in cancer cells appears to be different from its regulation control in certain rare survivin-positive human normal cells and tissues (3, 5). Thus, we have generated genetically modified cancer cell models from several cancer cell types for initial drug discovery and development. In these model cells, the modulation of luciferase activity by small chemical molecule compounds is expected to reflect the modulation of the endogenous expression of survivin. These cells are compatible with cell-based high throughput screening (HTS) formats for initial drug discovery and development (see FIG. 15 for overview of one embodiment of a drug discovery and development process according to the invention using the survivin gene as a target. Accordingly, the present invention is readily adaptable for high throughput screening of drug candidates.

The present invention is illustrated by the following examples which are not intended to limit the invention.

EXAMPLE 1

Selecting the correct survivin regulatory sequence that is believed to contain all of the necessary components for use as a promoter to drive exogenous reporter gene expression is important for drug discovery that uses reporter activity as a read-out to reflect the effect of test agents on the modulation of survivin expression. In this regard, we have successfully identified and cloned a 4.08-kb survivin promoter sequence, which is believed to accurately emulate the behavior of the endogenous survivin gene (both cell cycle-dependent and cell cycle-independent control of survivin transcription). This promoter was inserted upstream of the firefly luciferase reporter gene. The detailed isolation of the 4.08-kb survivin promoter region and its cloning was performed as follows.

Figure 2:
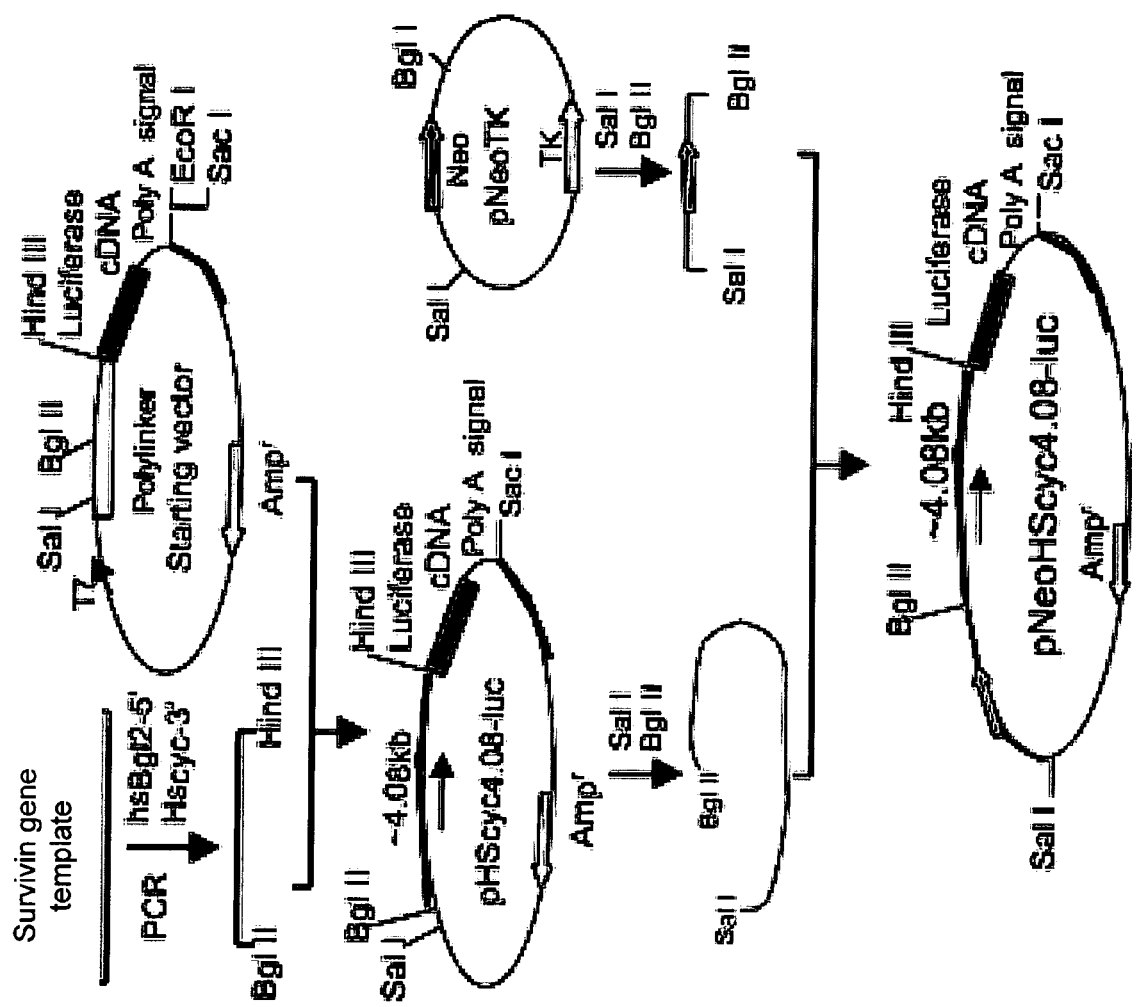
FIG. 2 provides a diagram of the generation of pNeoHScyc4.08-luc expression vector FIG. 3 provides a diagram of the generation of pNeoHS4.04-luc expression vector

Using the human survivin gene (GenBank accession number: U75285) as a template (FIG. 1), we amplified the 4.08-kb survivin promoter region (+1 to −4080 bp, the 'A' in the 'ATG' translation start site of the survivin gene is designated as +1) by PCR using the primer set (FIG. 1) of hsBgl2-5' (5'-GGAAAGATCTGTTCGCCTGACATC-3' (SEQ ID NO:2), the Bgl II site is italicized) and HScyc-3' (5'-CCCAAGCTTTGCCGCCGCCGCCACCTCTGCCAACG-3' (SEQ ID NO:3), Hind III for the cloning purpose is italicized). After digestion of the 4.08-kb PCR DNA fragment with Bgl II and Hind III restriction enzymes, the DNA fragment was cloned upstream of the luciferase gene at the Bgl II and Hind III sites of a novel starting vector to generate the intermediate vector, pHScyc4.08-luc (FIG. 2). The sequence for the survivin gene promoter in the pHScyc4.08-luc is presented in FIG. 4 and is provided as SEQ ID NO:1.

Next, a ~1.7-kb neomycin gene cassette (PGK-promoter-neomycin phosphotransferase-BGH-polyA signal) was isolated from the pNeoTK vector by Sal I and Bgl II, and cloned upstream of the 4.08-kb survivin promoter sequence in pHScyc4.08-luc. This final construct was designated as pNeoHScyc4.08-luc (FIG. 2).

Figure 3:
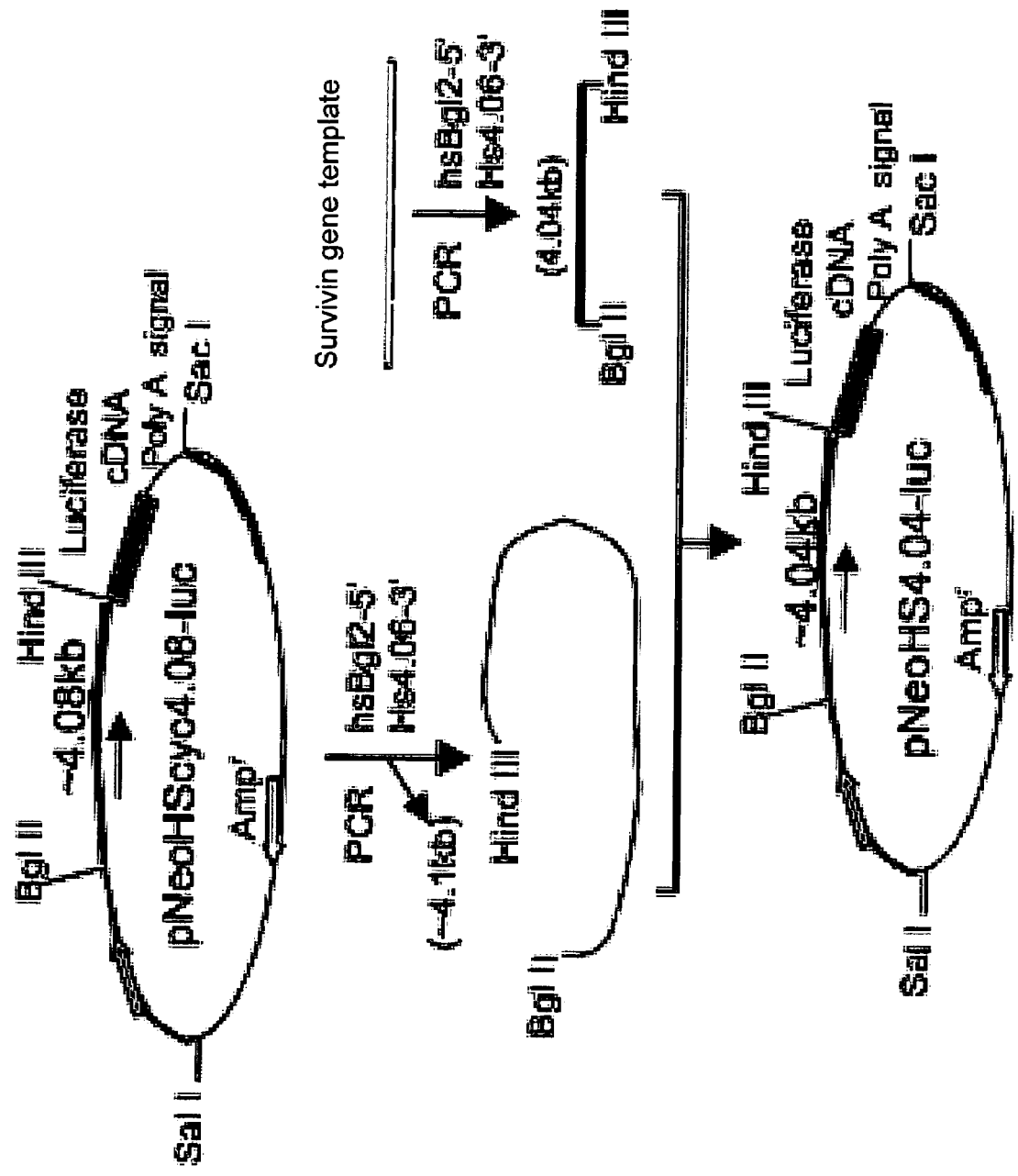

In order to have cancer cell-based systems to discover antitumor drugs which employ cell cycle-independent mechanisms to modulate survivin expression, we generated a cell cycle-independent survivin promoter-luciferase construct without the defined 38-bp DNA element (nucleotides −1 to −38 of FIG. 4). The strategy to create this expression vector is shown in FIG. 3. Briefly, we amplified the 4.04-kb human survivin promoter region by PCR using the primer set (FIG. 1) of hsBgl2-5' and HS4.04-3' (5'-CCCAAGCTTAAATCTGGCGGTTAATGGCG-3' (SEQ ID NO:4), the Hind III site for the cloning purpose is italicized). After digestion of the 4.04-kb PCR DNA fragment with Bgl II and Hind III, we replace the 4.08-kb survivin promoter DNA sequences in the pNeoHScyc4.08-luc expression vector with the 4.04-kb PCR DNA fragment as diagrammed in FIG. 3. We named this resultant expression vector pNeoHS4.04-luc, which lacks cell cycle-associated survivin transcription control. Thus, the effect of a test agent on cell cycle distribution will not affect luciferase activity in the cells transfected with pNeoHS4.04-luc.

EXAMPLE 2

This Example demonstrates the generation of cancer cells stably transfected with a human survivin promoter sequence in operable linkage with a reporter gene, and the use of such cells to evaluate the effect of various test agents on expression of the reporter gene. To obtain such cells, pNeoHScyc4.08-luc and pNeoHS4.04-luc were linearized with the Sal I restriction enzyme between the bacterial vector bone and the neomycin gene cassette (FIGS. 2 and 3). The linearized DNAs were transfected into various types of cancer cells, including breast, colon, prostate, lung and ovarian, respectively. Through a carefully designed G418 selection process, we isolated 100-300 single cell clones from each cancer cell type expressing either pNeoHScyc4.08-luc or pNeoHS4.04-luc to determine luciferase expression using luciferase activity assay. We found that 5-15% of cell clones show 1 to 3 orders of increased luciferase activity as compared with the negative control cells transfected with the promoterless empty vector (150-300 units/10 sec per 10-µl cell lysate).

Methods for transfection, G418 selection, single clone isolation and amplification: Cells were first tested for G418 resistance with a series of G418 concentrations. For transfection, cells were seeded in a 6-well cell culture plate, one day before transfection, to a cell concentration in which cell would grow into 40-70% confluence on the second day for transfection. Cells were transfected with the Sal I-linearized pNeoHScyc4.08-luc or pNeoHS4.04-luc using LIPOFECTAMINE™ 2000 (INVITROGEN). Briefly, 1-2 µg (dependent on cell transfection efficiency) of the linearized plasmid DNA in 100 µl serum-free DMEM were mixed with 1.5-3 µl Lipofectamine™ 2000 in 100 µl serum-free DMEM in a 1.5-ml tube for each well of 6-well plates. After incubation at room temperature for 20-25 minutes, the DNA/Lipofectamine™ 2000 mixture was added to each well containing 500 µl serum-free DMEM medium in the 6-well plate. Following 3-5 hour incubation in the $CO_2$ incubator, the DNA/Lipofectamine™ 2000 complex was replaced by complete medium containing 10% serum, and cells were incubated for additional 16-24 hours. Cells in each well of the 6-well plate were then diluted into 5-15 96-well plates with the corresponding cell culture medium containing an appropriate G418 concentration. Cell culture medium was replaced every 3-5 days with new medium containing the appropriate G418 concentration until cell clones appeared and grew to a sufficient size. Single cell clones in each well can be transferred into 96-well plates in duplicate. One copy of the 96-well plate can be used for testing luciferase activity in each well and the other 96-well plate as a reservoir of cell clones of interest.

Methods for measuring luciferase activity and isolation of the correct cell clones: For luciferase assays, the Luciferase Reporter Assay System (PROMEGA) was used. Transfected cell clones in 96-well plates were washed with PBS and lysed with 50 µl ·1× passive lysis buffer on a shaker for up to 1 hour at 4° C. Cell lysate was used for measurement of luciferase activities in a luminometer by mixing the cell lysate (10 µl) with 10 µl of the 1× luciferase assay reagent. Cell clones with 20-fold luciferase increases or more (about 5000 or more) were selected for further testing of luciferase expression stability over a 3-4 month period of continuously passing in the presence of an appropriate concentration of G418. Sub-culture/passage of each selected clone was performed every 7 days. Luciferase activity for each cell clones was determined every 4-5 sub-culture/passing. The cell clones with stable luciferase expression were tested for their response to treatments with various test agents that are known to modulate the expression of survivin.

Testing and verification of the selected cell clones responding to various drug treatments: The finally selected cell clones with high and stable luciferase expression were used for testing the effect of various test agents on luciferase activity. While certain test agents are employed in the Examples herein, other agents are also suitable for use in the invention. For example, test agents that may downregulate survivin expression include but are not limited to SN-38, the active form of CPT-11/irinotecan; Resveratriol, a natural diet product showing chemopreventive and antitumor activity; Selenium compounds such as Se-methylseleno-L-cysteine (MSC), methylseleninic acid (MSA); Vitamin D compounds; ligands with broad cancer chemopreventive and chemotherapeutic effects; Hedamycin, a GC rich sequence-selective DNA binding drug with antitumor activity; Retinoic acid, a natural diet product with broad cancer chemopreventive and chemotherapeutic effects; Dexamethasome; a natural diet product with broad cancer chemopreventive and chemotherapeutic effects; Silibinin/silybin/silymarin, a natural diet product with broad cancer chemopreventive and chemotherapeutic effects; Curcumin, a natural diet product with broad cancer chemopreventive and chemotherapeutic effects; AITC ((allyl isothiocyanate), a natural diet component with antitumor activity.

Antitumor drugs or other ligands that induce survivin expression as a drug resistant factor may include Taxol/paclitaxel, a broadly used antitumor drug in the clinic; Hoechst33342, an AT rich sequence-selective DNA binding drug with antitumor activity; and T138067, a novel antitumor drug, which has better effects than taxol on MDR-tumors.

We have shown that hedamycin, a GC rich sequence-selective DNA binding antitumor agent, inhibits survivin expression and downregulates survivin promoter activity in cancer cells (15). Therefore, we used Hedamycin as a positive control to test our genetically modified cancer cell models. We have determined that downregulation of survivin expression by hedamycin is a relative early event as compared to hedamycin-induced cancer cell death, and also cancer cells treated with 10 nM hedamycin for 16-24 hours do not show significant cell death. Thus, we have a useful window in which to test whether hedamycin downregulates luciferase reporter gene expression in our genetically modified cancer cell models. That is, the testing condition employed included 10 nM of hedamycin treatment for up to 24 hours, followed by measuring luciferase activity. This protocol was intended to avoid downregulation of survivin promoter/luciferase activity resulting from hedamycin-induced cell death. Using these testing conditions, equal cells per well were seeded in 96-well plates without using the edge wells 24 hours before hedamycin treatment. The confluence of cells at the time of hedamycin treatment was approximately 50-60%. After cells were treated with 10 nM hedamycin for 16-24 hours, cells were lysed and luciferase activity was measured as described above. Examples of responses in these experiments are shown in FIGS. 5-8. As can be seen from these figures, hedamycin significantly inhibited the luciferase activity in the various cancer cells tested.

We have also demonstrated that a AT rich sequence-selective DNA binding ligand, Hoechst33342 binds to the survivin promoter and upregulates the survivin promoter activity and endogenous survivin gene expression. Thus, we demonstrated the use of Hoechst33342 as a positive control for increased luciferase activity in our cancer cell model. We used 500 nM of Hoechst33342 to treat cells for 16-24 hours as above, at which we have demonstrated does not result in significant cell death. After treatment, cell lysis and luciferase activity assays were performed as described above. We demonstrated that Hoechst33342 upregulates survivin promoter/luciferase activity. Results are presented in FIGS. 9-12. Thus, we have demonstrated that the present genetically modified cancer cell models reflect endogenous human survivin gene expression in response to various drug treatments.

Interestingly, it is noted that survivin promoter/luciferase activity responses to drug treatment has no apparent relationship with the constitutive luciferase expression level in the tested cell clones. Thus, cell clones with appropriate responses to test agents were selected and amplified by expanding cell culture and depositing in liquid nitrogen as a source of cells for various applications, including the high-throughput screening. In addition, cancer cell clones transfected with the cell cycle-independent survivin promoter-luciferase constructs were also tested with both hedamycin and hoechst33342. Similar results were obtained. Illustrative results are presented in FIGS. 13-14.

EXAMPLE 3

This Example describes the utility of the invention in connection with high-throughput screening (HTS) techniques.

Performance of HTS with small chemical compound libraries is expected to identify drug candidates that inhibit (candidates for anticancer drugs) and induce (candidates for apoptosis-associated disease drugs) luciferase/survivin expression.

We used our A549 lung cancer model cells to illustrate one embodiment of HTS according to the invention. In general, 384-well plates are preferred for HTS. The A549 model cells can be easy to grow into mono-layers and trypsinized without any special care. The cell morphology in various conditions is shown in FIG. 16. It is preferable to maintain Human A549 lung cancer in Dulbecco's modified Eagle's medium (DMEM) containing 100 units/ml of penicillin & streptomycin and 10% fetal bovine serum in a 5% CO2 incubator at 37° C. Since this is a genetically modified cell line, it is also preferable to add G418 at a concentration of 400-500 ug/ml G418 to maintain stability. G418 may be omitted during screening.

For HTS, in one embodiment, equal amounts of A549 model cells can be seeded in 384-well plates for growing overnight, and one test agent added into each well for 24 hours, after which luciferase activity can be determined. Controls, such as wells without test compounds, and wells with positive control drugs (such as hedamycin can be used here) may be included. Suitable luciferase substrates are commercially available, such as from PROGMEGA, and luciferase expression assays can be performed according to standard techniques. It is noteworthy that the A549 cell grows very fast and doubling time is about 18-24 hours with unlimited passages. For example, if the cells are split from 90% confluence, then seeded at a ratio of one in ten, they can reach 90% confluence within about 3 to 4 days. The drug candidates identified from HTS can be tested for their effects on, for example, cancer cells (high survivin expression) growth and apoptosis induction versus normal [such as human dermal fibroblast (HDF) and NIH3T3 cells] and cancer cells without or with a very low level (such as MCF-10A) of survivin expression. Further validation of the efficacy of the test agents identified as being capable of modulating survivin expression can be performed according to standard techniques

EXAMPLE 4

This Example demonstrates the generation of a human survivin promoter-luciferase gene-transgenic (SPlucTg) mouse model and provides examples of its application in preclinical drug development Generation of SPlucTg mice: The targeting construct, pHScyc4.08-luc, was digested with Sal I and Sac I to isolate the 8.5 kb transgene cassette (HScyc4.08-luc) from the bacterial plasmid backbone (see FIG. 2). This is important because inclusion of the prokaryotic sequences in the generation of transgenic mice has been shown to induce deleterious methylation after random integration into the mouse genome. Cesium chloride-purified HScyc4.08-luc DNA was microinjected into the pronuclei of day-0.5 embryos of C57BL/6 mice. Injected embryos were implanted into the oviducts of pseudo-pregnant female Swiss Webster mice. Tail biopsies and subsequent DNA isolation was done when the resulting pups were 3 to 4 weeks of age for genotype analysis.

Presence of the transgene cassette was identified by PCR amplification of both the human survivin gene promoter and the luciferase gene sequence as shown (FIG. 17A). Two human survivin promoter-specific primers (that do not recognize the endogenous mouse survivin gene sequence), P1 (GCA GGA GAA TCG CTT GAA CCC GTG G; SEQ ID NO:5) and P2 (CCA CTC ACT TCT CTG GTT CTA TGG CC; SEQ ID NO:6), were used to amplify a 308-bp PCR product (FIG. 17A). Two firefly luciferase gene-specific primers, P3 (GTG GAT TAC GTC GCC AGT CAA GTA AC; SEQ ID NO:7) and P4 (CAA TAG CTA AGA ATT TCG TCA TCG CTG; SEQ ID NO:8), were used to amplify a 200-bp PCR product (FIG. 17A). A total of 20 offspring were born from 344 microinjected eggs, and out of these, 5 SPlucTg founder mice were identified [5190m, 5194f, 5195m, 5196m and 5197f, (FIG. 17B), m: male; f: female]. However, one (5194f) of the five founders did not pass the transgene to its progeny since no transgene-positive F1 offspring (zero out of 10) was identified from breeding this founder with C57BL/6 mice. In contrast, 4/11 F1 offspring from the 5190m founder mouse, 6/17 F1 from the 5195m founder, 5/12 F1 from the 5196m founder, and 5/8 F1 from the 5197f founder were transgene positive (m: male; f: female).

Figure 18:
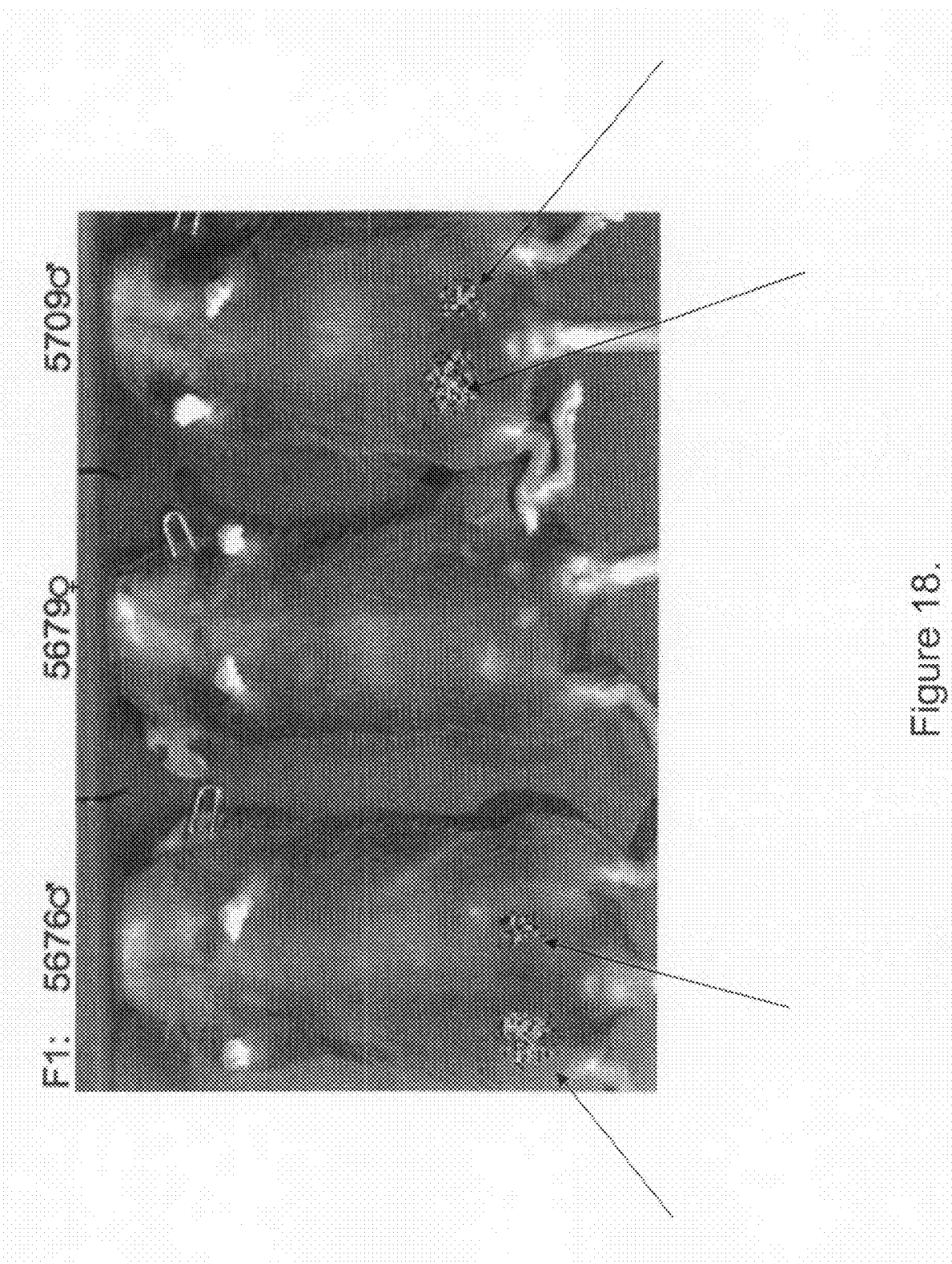
FIG. 18 is a photographic representation of luciferase expression profile in SPlucTg mice obtained using the XENOGEN IVIS® in vivo Imaging System (arrows indicate luciferase expression).

Using a survivin-specific monoclonal antibody termed 12C4, we have recently shown that testis is the only human organ that highly expresses survivin (60-70% of spermatogonia) (19). Consistent with this observation, luciferase activity in SPlucTg mice was detected only in the testis of male mice but not in female mice (founder, F1 and F2). Luciferase activity was assayed by whole body imaging using the XENOGEN IVIS® in vivo Imaging System. Examples from three F1 SPlucTg mice are shown in FIG. 18.

Figure 19:
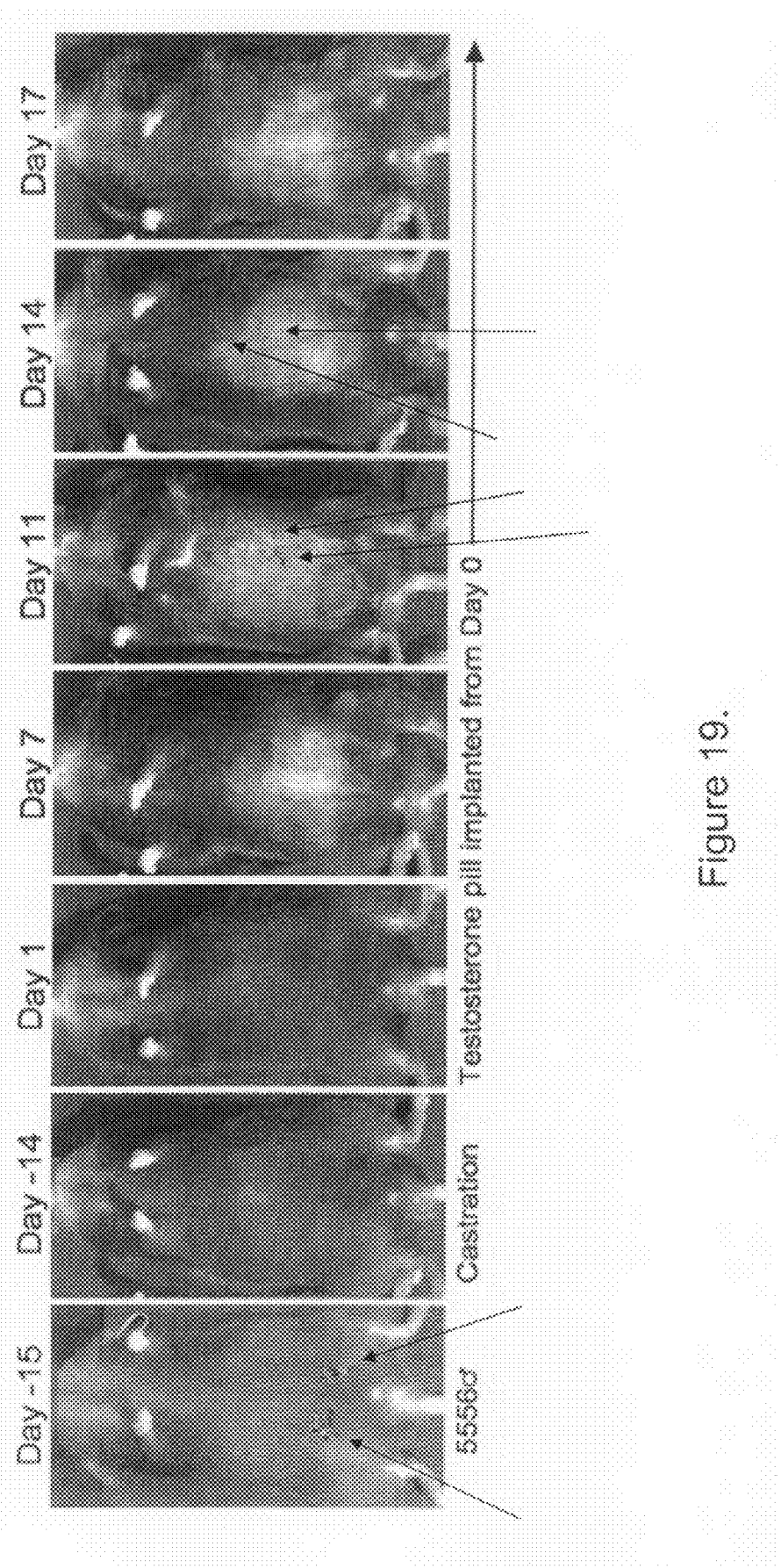
FIG. 19 is a photographic representation (obtained using the XENOGEN IVIS® in vivo Imaging System) of transient turn-on of survivin promoter activity by imbedding testosterone pills in castrated SPlucTg mice: Testosterone pills were imbedded in the back of the neck of SPlucTg mice (an example shown here is the F1 5556m derived from 5196m founder) 14 days after castration (prostate tissue shrinking to the minimal size by apoptosis in the 14 days). After testosterone pill implantation, luciferase activity was monitored using in vivo imaging. The image at Day-15 is before castration, two testes show luciferase activity, suggesting that the human survivin promoter is active. Transient induction of survivin promoter activity was seen on Day 11 and Day 14 post pill imbedding (arrows indicate luciferase expression).

Transient luciferase activity was detected during mouse prostate tissue proliferation induced by androgen treatment of castrated SPlucTg male mice: Growing evidence indicates that the regulation of survivin constitutive expression in normal tissue (transient) is different from that in cancer tissues (3). This is consistent with the fact that survivin transient expression is required for physiological cell proliferation after such as tissue injury or hormone stimulation. We found a transient luciferase activity induced by androgen treatment of castrated SPlucTg male mice (FIG. 19). This experiment indicates that the survivin promoter-driven transgene in SPlucTg mice could be activated.

Figure 20:
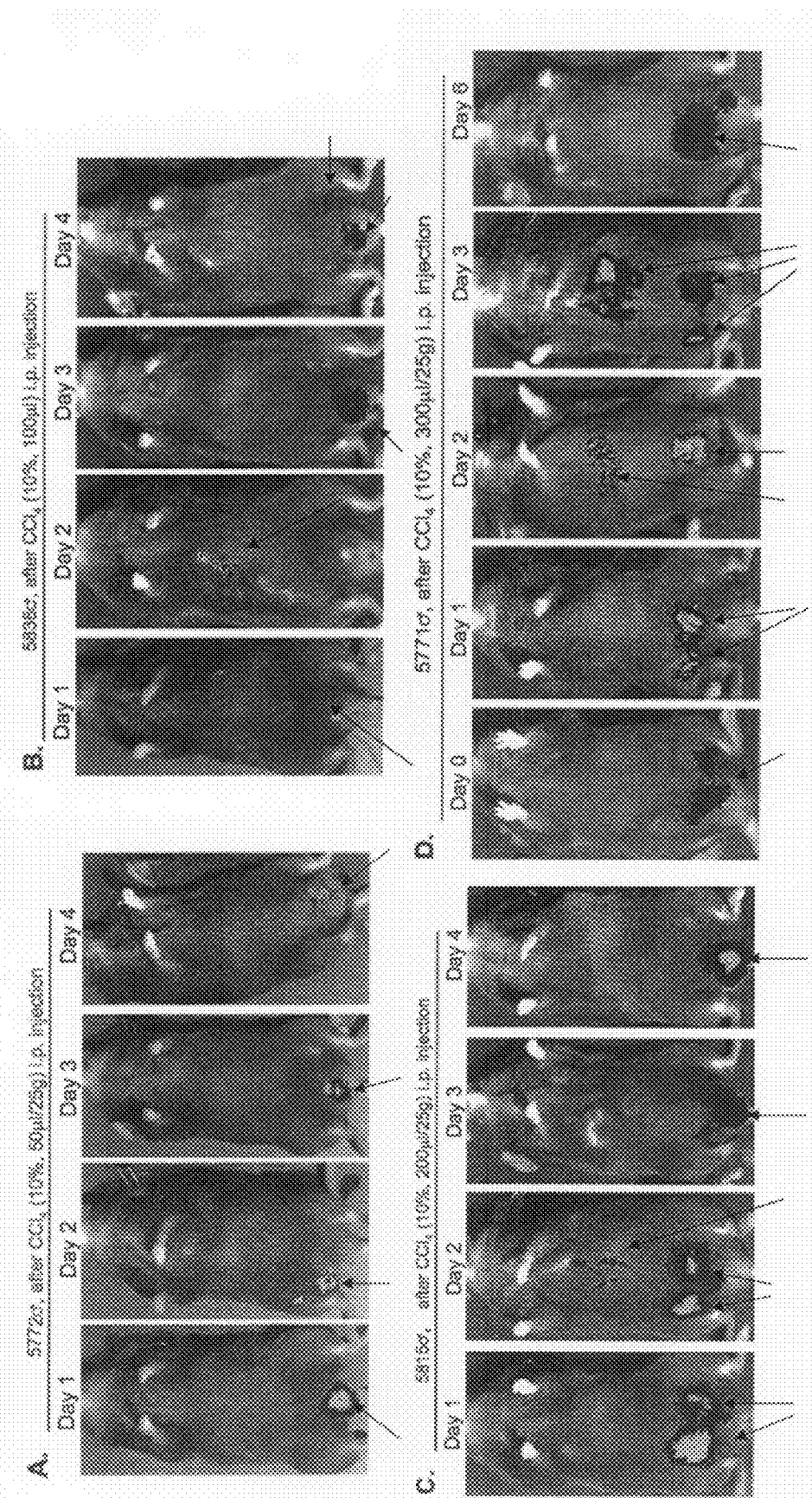
FIG. 20 is a photographic representation (obtained using the XENOGEN IVIS® in vivo Imaging System) of dose-dependent transient turn-on of survivin promoter activity during SPlucTg mouse liver injury and regeneration using carbon tetrachloride (CCl4): A 10% of CCl4 solution formulated in corn oil was prepared. The following dose was injected intraperitoneally on Day 0: 50 µl/25 g (panel A), 100 µl/25 g (panel B), 200 µl/25 g (panel C) and 300 µl/25 g (panel D). The in vivo imaging was monitored on Day 1 (24 h), Day 2 (48 h), Day 3 (72 h), Day 4 (96 h) and Day 6 (144 h) after administration of CCl4 (arrows indicate luciferase expression).

Although normal adult liver tissues do not express survivin, previous studies demonstrated that the expression of survivin is turned on during mouse liver regeneration after carbon tetrachloride (CCl4)-inducing liver injury (20). Based on this observation, we tested whether we could observe luciferase activity during mouse liver regeneration after injury. We observed strong luciferase activity, which delineates the outline of the mouse liver position and form, during liver regeneration after intraperitoneal injection of CCl4 to induce mouse liver injury (FIG. 20). Thus, this SPlucTg mouse model appears to accurately reflect the endogenous survivin gene activity. Importantly, the mouse liver injury and luciferase activity monitored by in vivo imaging is CCl4 dose-dependent, which provides a novel basis for testing compound-induced tissue injury/toxicity.

Figure 21:
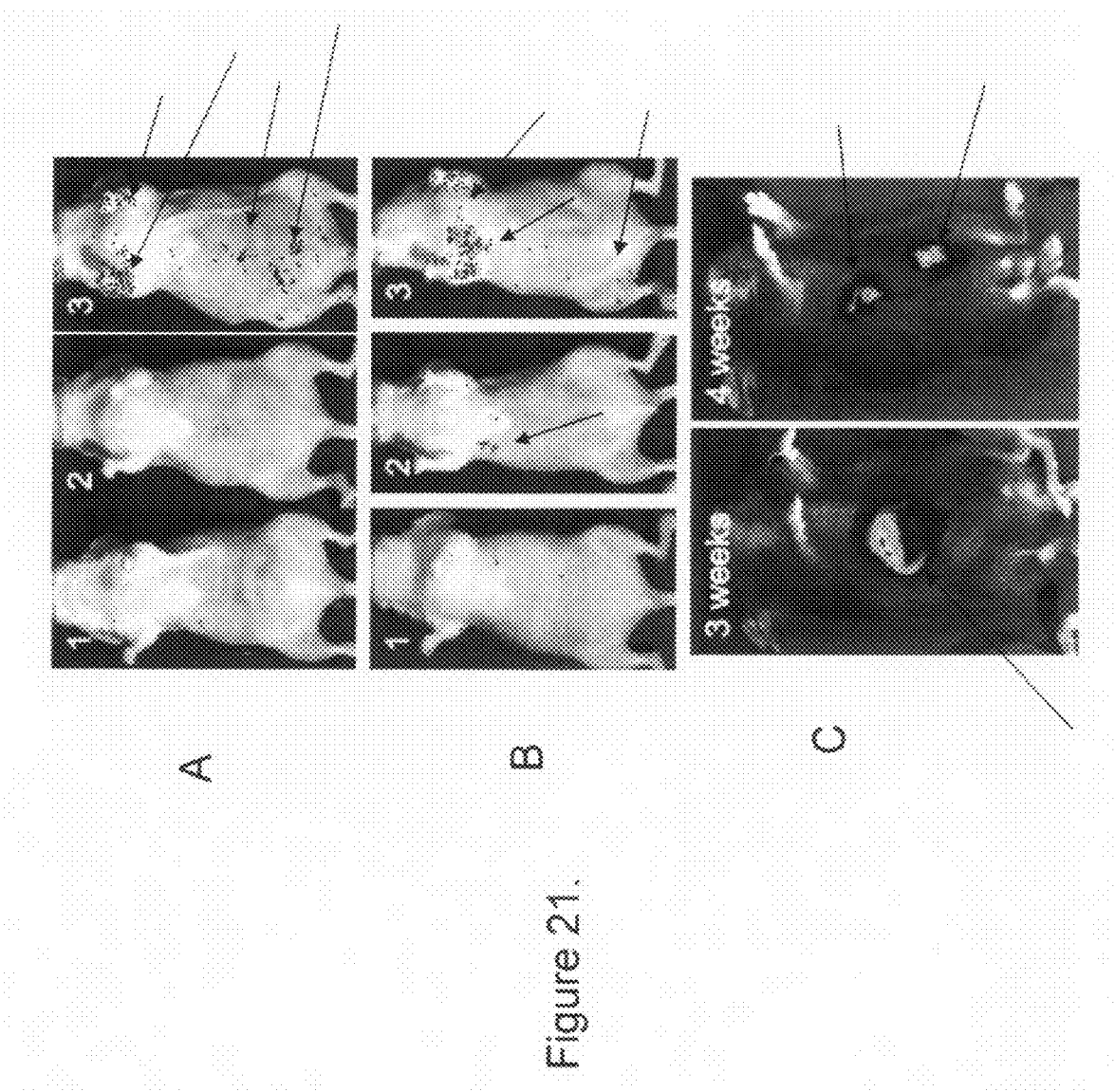
FIG. 21 is photographic representation (obtained using the XENOGEN IVIS® in vivo Imaging System) of the metastatic and xenograft mouse tumor models monitored through in vivo imaging: Cancer cells as labeled were injected into the mouse circulation via tail vein injection (A, B and C4) or subcutaneous injection (C3). Tumor cell distribution (A, B and C4) and growth (A, B and C) were monitored weekly using the IVIS® in vivo Imaging System. We found that injected cells could not be detected after one week (A1, B1). However, cancer cells began to form tumor cell colonies in specific area of mouse body after three weeks (A3, B3), which was dependent on the aggressiveness of the cancer cell type. For example, E0771 cell is very aggressive and formed tumors very fast (arrows indicate luciferase expression).

Monitoring cancer initiation, progression and metastasis in living mice by bioluminescence in vivo imaging: One way to monitor survivin expression in an in vivo animal model during cancer initiation, progression and metastasis is to use our genetically modified cancer cells described in this invention above for drug discovery and development. Here we demonstrate the ability to monitor luciferase activity (reflected survivin expression) and to follow tumor cell distribution/growth by in vivo imaging using a metastatic mouse model. Human survivin promoter luciferase-stably transfected ovarian cancer P11-SPluc cells (FIG. 21A), human survivin promoter luciferase-stably transfected prostate cancer PC3-SPluc cells (FIG. 21B) and human survivin promoter luciferase-stably transfected murine breast cancer E0771-SPluc cells (FIG. 21C), were injected from the tail vein into the mouse circulation. Tumor cell distribution/growth and metastasis were monitored using whole body in vivo imaging (FIG. 21). Thus, it will be recognized by those skilled in the art that a transgenic mouse having therein a human survivin promoter and a reporter gene is useful for screening test agents for the capability to modulate transcription from the survivin promoter. In this regard, with respect to drug toxicity evaluation, liver toxicity is a critical parameter to the fate of a drug candidate evaluated by the FDA. The data from FIG. 20 indicate that liver tissue injury strongly activates luciferase activity (reflecting survivin expression). Thus, it is expected that we can use our SPlucTg mice to easily monitor normal tissue injury such as liver injury induced by drug toxicity through in vivo luciferase imaging. Further, we also expect to be able to analyze testing agents by crossing our SPlucTg mice with a tumor mouse model, such as with the TRAMP [transgenic adenocarcinoma of the mouse prostate (21)] mouse model, with the expectation that the offspring produced in this way will be a viable tool for testing drug efficacy in the inhibition of tumor initiation, growth and metastasis through in vivo whole animal body imaging. The SPluc model cells could also be used to create a metastatic model, as we demonstrated in FIG. 21, to test drug efficacy.

REFERENCES

1. Li, F. J Cell Physiol, 197: 8-29, 2003.
2. Li, F. and Ling, X. J Cell Physiol, 208: 476-486, 2006.
3. Li, F. and Brattain, M. G. Am J Pathol, 169: 1-11, 2006.
4. Li, F. Br J Cancer, 92: 212-216, 2005.
5. Zhang, M., Yang, J., and Li, F. J Exp Clin Cancer Res, 25: 391-402, 2006.
6. Li, F., et al. Nature, 396: 580-584, 1998.
7. Skoufias, et al. J Cell Biol, 151: 1575-1582, 2000.
8. Uren, et al. Curr Biol, 10: 1319-1328, 2000.
9. Dohi, et al. J Clin Invest, 114: 1117-1127, 2004.
10. Li, F., et al. Nat Cell Biol, 1: 461-466, 1999.
11. Reed, J. C. et al. Nat Cell Biol, 1: E199-200, 1999.
12. Li, F., et al. Oncogene, 24: 1385-1395, 2005.
13. Li, F. and Altieri, D. C. Cancer Res, 59: 3143-3151, 1999.
14. Li, F. and Altieri, D. C. Biochem J, 344 Pt 2: 305-311, 1999.
15. Wu, J., et al. J Biol Chem, 280: 9745-9751, 2005.
19. Spaulding, et al. Histopathology, 49: 622-633, 2006.
20. Deguchi, et al. Expression of survivin during liver regeneration. Biochem Biophys Res Commun, 297: 59-64, 2002.
21. Greenberg, et al. Proc Natl Acad Sci USA, 92: 3439-3443, 1995.

I claim:

1. An in vitro eukaryotic cell containing a DNA polynucleotide comprising a human survivin promoter sequence having SEQ ID NO:1 or SEQ ID NO:9, wherein the human survivin promoter sequence is operably linked to a reporter gene.

2. The eukaryotic cell of claim 1, wherein the reporter gene encodes luciferase.

3. The eukaryotic cell of claim 1, wherein the cell is a cancer cell stably transfected with the DNA polynucleotide of claim 1.

4. The cancer cell of claim 3, wherein the cell is a lung cancer cell, an ovarian cancer cell, a colon cancer cell, or a prostate cancer cell.

5. The eukaryotic cell of claim 1, wherein the cell is a mouse cell.

6. The eukaryotic cell of claim 1, wherein the human survivin promoter sequence consists of SEQ ID NO:1 or SEQ ID NO:9.

* * * * *

```
                       SEQUENCE LISTING

<160> NUMBER OF SEQ ID NOS: 9

<210> SEQ ID NO 1
<211> LENGTH: 4081
<212> TYPE: DNA
<213> ORGANISM: homo sapiens
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t

<400> SEQUENCE: 1
agatctgttc gcctgacatc ctgtttgagc ctgggtggac aggacagcac ctgccagcat      60
cgggaagcac tgcagatggg aagaggcttg gtcactctcc aaaggtggca ggagttggag     120
ggggtgagct gaaggtaagg agaaaggagg tggggaccca ggagacaggg gctgcgcagc     180
gggctcgggg ctgacacccc cacggataca gttcastggg gntcaaacat aaaaggaacc     240
caactattgt gggnggaaaa gactttytg cctttctgcc ttttcttntt ttcttttct      300 ttctttcttt ttttttttt tttttgaga cagagtcttg ttytatcgcc caggctggag     360
tgcagtggcg tgatctcggc tcactgcaag ctctgcctcc cgggatcacg ccattctcct     420
gcctcaacct cccgagcagc tgggactaca ggcgcctgcc accacacccg gstattttt      480
```

-continued

```
tgtattttt   agtagagatg   gggtttcacc   gtgttagcca   ggacggtctc   gatctcctga      540
ccttgtgatc  cgcccgcctc   ggcctyccaa   agtgctggga   ttacaggcgt   tgagccaccg      600
cgcctggctc  ttttttcttt   cttttttttt   ttccgagaca   gagtttcact   cttgttgccc      660
aggctggagt  gcagtggcgc   gatcttggct   cactgcaacc   tccacctnca   gggttcaagc      720
gattctcctg  cctcagcctc   ctgagtagct   gggactgcag   gcgcgcacca   ccacgcctgg      780
ctaattttg   tattttagt    agagacaggg   tttcaccata   ttggccaggc   tggtctcgaa      840
ctcctgacct  tgtgatctgc   ccacctcagc   ctcccaaagt   cctgggatta   caggcgtgag      900
ccaccgtgcc  cagcctgacc   cctctgccct   ttcaaaaact   atgttcgttc   tctcacagcc      960
ttctcttgtc  atattaagtc   cacaccgcag   gcctaatttg   tccagtgaat   gctatgcaaa     1020
tatttcatgc  acctgctgat   cgcaggaatg   atatgtactt   ggtacgcact   gatcgtacct     1080
cggggtggga  gaagagaggg   caaggaagca   aagaatagcc   ccctcctttc   ctggtgcacc     1140
ttcagatgtg  ccgatggggc   ccaggctcgc   tgcagatggc   cccccttccca  gagacagggg     1200
aggatcctcc  acccactccc   cagcctccag   gaccatcgtg   actcctgcct   tcaggcactc     1260
aagttatgcg  tctagacatg   cggatatatt   caagctgggc   acagcacagc   agccccaccc     1320
caggcagctt  gaaatcagag   ctggggtcca   aagggaccac   accccgaggg   actgtgtggg     1380
ggtcgggggca cacaggccac   tgcttccccc   cgtctttctc   agccattcct   gaagtcagcc     1440
tcactctgct  tctcagggat   ttcaaatgtg   cagagactct   ggcacttttg   tagaagcccc     1500
ttctggtcct  aacttacacc   tggatgctgt   ggggctgcag   ctgctgctcg   ggctcgggag     1560
gatgctgggg  gcccggtgcc   catgagcttt   tgaagctcct   ggaactcggt   tttgagggtg     1620
ttcaggtcca  ggtggacacc   tgggctgtcc   ttgtccatgc   atttgatgac   attgtgtgca     1680
gaagtgaaaa  ggagttaggc   cgggcatgct   ggcttatgcc   tgtaatccca   gcactttggg     1740
aggctgaggc  gggtggatca   cgaggtcagg   agttcaatac   cagcctggcc   aagatggtga     1800
aaccccgtct  ctactaaaaa   tacaaaaaaa   ttagccgggc   atggtggcgg   gcgcatgtaa     1860
tcccagctac  tggggggggct  gaggcagaga   attgctggaa   cccaggagat   ggaggttgca     1920
gtgagccaag  attgtgccac   tgcactgcac   tccagcctgg   cgacagagca   agactctgtc     1980
tcaaaaaaaa  aaaaaaaaag   tgaaaaggag   ttgttccttt   cctccctcct   gagggcaggc     2040
aactgctgcg  gttgccagtg   gaggtggtgc   gtccttggtc   tgtgcctggg   ggccacccca     2100
gcagaggcca  tggtggtgcc   agggcccggt   tagcgagcca   atcagcagga   cccaggggcg     2160
acctgccaaa  gtcaactgga   tttgataact   gcagcgaagt   taagtttcct   gattttgatg     2220
attgtgttgt  ggttgtgtaa   gagaatgaag   tatttcgggg   tagtatggta   atgccttcaa     2280
cttacaaacg  gttcaggtaa   accacccata   tacatacata   tacatgcatg   tgatatatac     2340
acatacaggg  atgtgtgtgt   gttcacatat   atgaggggag   agagactagg   ggagagaaag     2400
taggttgggg  agagggagag   agaaaggaaa   acaggagaca   gagagagagc   ggggagtaga     2460
gagagggaag  gggtaagaga   gggagaggag   gagagaaagg   gaggaagaag   cagagagtga     2520
atgttaaagg  aaacaggcaa   aacataaaca   gaaaatctgg   gtgaagggta   tatgagtatt     2580
ctttgtacta  ttcttgcaat   tatctttat    ttaaattgac   atcgggccgg   gcgcagtggc     2640
tcacatctgt  aatcccagca   ctttgggagg   ccgaggcagg   cagatcactt   gaggtcagga     2700
gtttgagacc  agcctggcaa   acatggtgaa   accccatctc   tactaaaaat   acaaaaatta     2760
gcctggtgtg  gtggtgcatg   cctttaatct   cagctactcg   ggaggctgag   gcaggagaat     2820
```

-continued

```
cgcttgaacc cgtggcgggg aggaggttgc agtgagctga gatcatgcca ctgcactcca    2880
gcctgggcga tagagcgaga ctcagtttca aataaataaa taaacatcaa aataaaaagt    2940
tactgtatta aagaatgggg gcggggtggg aggggtgggg agaggttgca aaaataaata    3000
aataaataaa taaaccccaa aatgaaaaag acagtggagg caccaggcct gcgtgggct     3060 ggagggctaa taaggccagg cctcttatct ctggccatag aaccagagaa gtgagtggat    3120
gtgatgccca gctccagaag tgactccaga acaccctgtt ccaaagcaga ggacacactg    3180 atttttttt taataggctg caggacttac tgttggtggg acgccctgct ttgcgaaggg     3240
aaaggaggag tttgccctga gcacaggccc ccacccccca ctgggctttc ccagctccc     3300 ttgtcttctt atcacggtag tggcccagtc cctggcccct gactccagaa ggtggccctc    3360
ctggaaaccc aggtcgtgca gtcaacgatg tactcgccgg acagcgatg tctgctgcac     3420 tccatccctc ccctgttcat ttgtccttca tgcccgtctg gagtagatgc ttttgcaga     3480 ggtggcaccc tgtaaagctc tcctgtctga cttttttttt tttttagac tgagtttgc      3540 tcttgttgcc taggctggag tgcaatggca caatctcagc tcactgcacc ctctgcctcc    3600
cgggttcaag cgattctcct gcctcagcct cccgagtagt tgggattaca ggcatgcacc    3660
accacgccca gctaatttt gtattttag tagagacaag gtttcaccgt gatggccagg      3720
ctggtcttga actccaggac tcaagtgatg ctcctgccta ggcctctcaa agtgttggga    3780
ttacaggcgt gagccactgc acccggcctg cacgcgttct ttgaaagcag tcgagggggc    3840
gctaggtgtg ggcagggacg agctggcgcg cgtcgctgg gtgcaccgcg accacgggca     3900
gagccacgcg gcgggaggac tacaactccc ggcacacccc gcgccgcccc gcctctactc    3960
ccagaaggcc gcggggggtg gaccgcctaa gagggcgtgc gctcccgaca tgccccgcgg    4020
cgcgccatta accgccagat ttgaatcgcg ggacccgttg gcagaggtgg cggcggcggc    4080
a                                                                   4081
```

```
<210> SEQ ID NO 2
<211> LENGTH: 24
<212> TYPE: DNA
<213> ORGANISM: Artificial Sequence
<220> FEATURE:
<223> OTHER INFORMATION: PCR primer

<400> SEQUENCE: 2
ggaaagatct gttcgcctga catc                                          24

<210> SEQ ID NO 3
<211> LENGTH: 35
<212> TYPE: DNA
<213> ORGANISM: Artificial Sequence
<220> FEATURE:
<223> OTHER INFORMATION: PCR primer

<400> SEQUENCE: 3
cccaagcttt gccgccgccg ccacctctgc caacg                              35

<210> SEQ ID NO 4
<211> LENGTH: 29
<212> TYPE: DNA
<213> ORGANISM: Artificial Sequence
<220> FEATURE:
<223> OTHER INFORMATION: PCR primer

<400> SEQUENCE: 4
cccaagctta atctggcgg ttaatggcg                                      29
```

<210> SEQ ID NO 5
<211> LENGTH: 25
<212> TYPE: DNA
<213> ORGANISM: Artificial Sequence
<220> FEATURE:
<223> OTHER INFORMATION: PCR primer

<400> SEQUENCE: 5
gcaggagaat cgcttgaacc cgtgg                                    25

<210> SEQ ID NO 6
<211> LENGTH: 26
<212> TYPE: DNA
<213> ORGANISM: Artificial Sequence
<220> FEATURE:
<223> OTHER INFORMATION: PCR Primer

<400> SEQUENCE: 6
ccactcactt ctctggttct atggcc                                   26

<210> SEQ ID NO 7
<211> LENGTH: 26
<212> TYPE: DNA
<213> ORGANISM: firefly

<400> SEQUENCE: 7
gtggattacg tcgccagtca agtaac                                   26

<210> SEQ ID NO 8
<211> LENGTH: 27
<212> TYPE: DNA
<213> ORGANISM: firefly

<400> SEQUENCE: 8
caatagctaa gaatttcgtc atcgctg                                  27

<210> SEQ ID NO 9
<211> LENGTH: 4042
<212> TYPE: DNA
<213> ORGANISM: homo sapiens
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t

<400> SEQUENCE: 9
agatctgttc gcctgacatc ctgtttgagc ctgggtggac aggacagcac ctgccagcat    60
cgggaagcac tgcagatggg aagaggcttg gtcactctcc aaaggtggca ggagttggag   120
ggggtgagct gaaggtaagg agaaaggagg tggggaccca ggagacaggg gctgcgcagc   180
gggctcgggg ctgacacccc cacggataca gttcastggg gntcaaacat aaaaggaacc   240
caactattgt gggnggaaaa gactttytyg cctttctgcc ttttcttntt ttcttttttct   300

```
ttctttcttt ttttttttttt tttttttgaga cagagtcttg ttytatcgcc caggctggag      360
tgcagtggcg tgatctcggc tcactgcaag ctctgcctcc cgggatcacg ccattctcct      420
gcctcaacct cccgagcagc tgggactaca ggcgcctgcc accacacccg gstatttttt      480
tgtatttttt agtagagatg gggtttcacc gtgttagcca ggacggtctc gatctcctga      540
ccttgtgatc cgcccgcctc ggcctyccaa agtgctggga ttacaggcgt tgagccaccg      600
cgcctggctc tttttctttt cttttttttt ttccgagaca gagtttcact cttgttgccc      660
aggctggagt gcagtggcgc gatcttggct cactgcaacc tccacctnca gggttcaagc      720
gattctcctg cctcagcctc ctgagtagct gggactgcag gcgcgcacca ccacgcctgg      780 ctaattttttg tattttttagt agagacaggg tttcaccata ttggccaggc tggtctcgaa      840
ctcctgacct tgtgatctgc ccacctcagc ctcccaaagt cctgggatta caggcgtgag      900
ccaccgtgcc cagcctgacc cctctgccct ttcaaaaact atgttcgttc tctcacagcc      960
ttctcttgtc atattaagtc cacaccgcag gcctaatttg tccagtgaat gctatgcaaa     1020
tatttcatgc acctgctgat cgcaggaatg atatgtactt ggtacgcact gatcgtacct     1080
cggggtggga gaagagaggg caaggaagca aagaatagcc ccctcctttc ctggtgcacc     1140
ttcagatgtg ccgatggggc ccaggctcgc tgcagatggc cccttccca gagacagggg     1200 aggatcctcc acccactccc cagcctccag gaccatcgtg actcctgcct tcaggcactc     1260
aagttatgcg tctagacatg cggatatatt caagctgggc acagcacagc agccccaccc     1320
caggcagctt gaaatcagag ctggggtcca aagggaccac accccgaggg actgtgtggg     1380
ggtcggggca cacaggccac tgcttccccc cgtctttctc agccattcct gaagtcagcc     1440
tcactctgct tctcagggat ttcaaatgtg cagagactct ggcacttttg tagaagcccc     1500
ttctggtcct aacttacacc tggatgctgt ggggctgcag ctgctgctcg gctcgggag      1560 gatgctgggg gcccggtgcc catgagcttt tgaagctcct ggaactcggt tttgagggtg     1620
ttcaggtcca ggtggacacc tgggctgtcc ttgtccatgc atttgatgac attgtgtgca     1680
gaagtgaaaa ggagttaggc cgggcatgct ggcttatgcc tgtaatccca gcactttggg     1740
aggctgaggc gggtggatca cgaggtcagg agttcaatac cagcctggcc aagatggtga     1800
aaccccgtct ctactaaaaa tacaaaaaaa ttagccgggc atggtggcgg gcgcatgtaa     1860
tcccagctac tgggggggct gaggcagaga attgctggaa cccaggagat ggaggttgca     1920
gtgagccaag attgtgccac tgcactgcac tccagcctgg cgacagagca agactctgtc     1980
tcaaaaaaaa aaaaaaaaag tgaaaaggag ttgttccttt cctccctcct gagggcaggc     2040
aactgctgcg gttgccagtg gaggtggtgc gtccttggtc tgtgcctggg ggccaccccca     2100 gcagaggcca tggtggtgcc agggcccggt tagcgagcca atcagcagga cccaggggcg     2160
acctgccaaa gtcaactgga tttgataact gcagcgaagt taagtttcct gattttgatg     2220
attgtgttgt ggttgtgtaa gagaatgaag tatttcgggg tagtatggta atgccttcaa     2280
cttacaaacg gttcaggtaa accacccata tacatacata tacatgcatg tgatatatac     2340
acatacaggg atgtgtgtgt gttcacatat atgaggggag agagactagg ggagagaaag     2400
taggttgggg agagggagag agaaaggaaa acaggagaca gagagagagc ggggagtaga     2460
gagagggaag gggtaagaga gggagaggag gagagaaagg gaggaagaag cagagagtga     2520
atgttaaagg aaacaggcaa aacataaaca gaaaatctgg gtgaagggta tatgagtatt     2580
ctttgtacta ttcttgcaat tatctttttat ttaaattgac atcgggccgg gcgcagtggc     2640
tcacatctgt aatcccagca ctttgggagg ccgaggcagg cagatcactt gaggtcagga     2700
```

-continued

```
gtttgagacc agcctggcaa acatggtgaa accccatctc tactaaaaat acaaaaatta    2760
gcctggtgtg gtggtgcatg cctttaatct cagctactcg ggaggctgag gcaggagaat    2820
cgcttgaacc cgtggcgggg aggaggttgc agtgagctga gatcatgcca ctgcactcca    2880
gcctgggcga tagagcgaga ctcagtttca aataaataaa taaacatcaa aataaaaagt    2940
tactgtatta aagaatgggg gcggggtggg aggggtgggg agaggttgca aaaataaata    3000
aataaataaa taaaccccaa aatgaaaaag acagtggagg caccaggcct gcgtggggct    3060
ggagggctaa taaggccagg cctcttatct ctggccatag aaccagagaa gtgagtggat    3120
gtgatgccca gctccagaag tgactccaga acaccctgtt ccaaagcaga ggacacactg    3180
attttttttt taataggctg caggacttac tgttggtggg acgccctgct ttgcgaaggg    3240
aaaggaggag tttgccctga gcacaggccc ccaccctcca ctgggctttc cccagctccc    3300
ttgtcttctt atcacggtag tggcccagtc cctggcccct gactccagaa ggtggccctc    3360
ctggaaaccc aggtcgtgca gtcaacgatg tactcgccgg gacagcgatg tctgctgcac    3420
tccatccctc ccctgttcat ttgtccttca tgcccgtctg gagtagatgc ttttttgcaga   3480
ggtggcaccc tgtaaagctc tcctgtctga cttttttttt tttttttagac tgagttttgc   3540
tcttgttgcc taggctggag tgcaatggca caatctcagc tcactgcacc ctctgcctcc    3600
cgggttcaag cgattctcct gcctcagcct cccgagtagt tgggattaca ggcatgcacc    3660
accacgccca gctaattttt gtattttttag tagagacaag gtttcaccgt gatggccagg   3720
ctggtcttga actccaggac tcaagtgatg ctcctgccta ggcctctcaa agtgttggga    3780
ttacaggcgt gagccactgc acccggcctg cacgcgttct ttgaaagcag tcgagggggc    3840
gctaggtgtg ggcagggacg agctggcgcg gcgtcgctgg gtgcaccgcg accacgggca    3900
gagccacgcg gcgggaggac tacaactccc ggcacacccc gcgccgcccc gcctctactc    3960
ccagaaggcc gcgggggggtg gaccgcctaa gagggcgtgc gctcccgaca tgccccgcgg   4020
cgcgccatta accgccagat tt                                             4042
```